(12) United States Patent
Doty et al.

(10) Patent No.: US 11,471,315 B2
(45) Date of Patent: Oct. 18, 2022

(54) HEIGHT, DEPTH AND CIRCUMFERENTIAL ADJUSTMENT MECHANISMS FOR CERVICAL COLLAR

(71) Applicant: DJO, LLC, Vista, CA (US)

(72) Inventors: Alexis Doty, Carlsbad, CA (US); Tara VandenBerg, Rancho Santa Fe, CA (US); Robert Bejarano, Carlsbad, CA (US); Kevin Patrick Larmer, San Marcos, CA (US); J. Andrew Moulds, Encinitas, CA (US); Jeffrey M. Mullally, La Mesa, CA (US); Paul J. Klock, Carlsbad, CA (US)

(73) Assignee: DJO, LLC, Carlsbad, CA (US)

( * ) Notice: Subject to any disclaimer, the term of this patent is extended or adjusted under 35 U.S.C. 154(b) by 246 days.

(21) Appl. No.: 16/879,086

(22) Filed: May 20, 2020

(65) Prior Publication Data

US 2020/0368056 A1 Nov. 26, 2020

Related U.S. Application Data

(60) Provisional application No. 62/991,374, filed on Mar. 18, 2020, provisional application No. 62/939,496, filed on Nov. 22, 2019, provisional application No. 62/872,510, filed on Jul. 10, 2019, provisional application No. 62/850,971, filed on May 21, 2019, provisional application No. 62/850,984, filed on May 21, 2019, provisional application No. 62/851,028, filed on May 21, 2019, provisional application No. 62/851,023, filed on May 21, 2019, provisional application No. 62/850,958, filed on May 21, 2019.

(51) Int. Cl.
*A61F 5/05* (2006.01)
*A61F 5/055* (2006.01)
*A61F 5/01* (2006.01)

(52) U.S. Cl.
CPC ...... *A61F 5/055* (2013.01); *A61F 2005/0197* (2013.01)

(58) Field of Classification Search
CPC .............. A61F 5/055; A61F 2005/0197; A61F 5/05883
See application file for complete search history.

(56) References Cited

U.S. PATENT DOCUMENTS

| 2,820,455 | A | * | 1/1958 | Hall ........................ A61F 5/055 602/18 |
| 3,027,894 | A | | 4/1962 | Moore |
| 3,916,885 | A | | 11/1975 | Gaylord |

(Continued)

FOREIGN PATENT DOCUMENTS

| DE | 1024205 B | 2/1958 |
| KR | 20040043256 A | 5/2004 |

(Continued)

OTHER PUBLICATIONS

U.S. Appl. No. 62/850,958, filed May 21, 2019, Alexis Doty.

(Continued)

*Primary Examiner* — Camtu T Nguyen
(74) *Attorney, Agent, or Firm* — Veros Legal Solutions, LLP

(57) ABSTRACT

Cervical collars, components thereof, and methods of using them overcome issues with conventional cervical collars.

14 Claims, 25 Drawing Sheets

(56) References Cited

U.S. PATENT DOCUMENTS

| | | | |
|---|---|---|---|
| 4,582,051 A | 4/1986 | Greene et al. | |
| 5,433,696 A | 7/1995 | Osti | |
| 5,593,382 A | 1/1997 | Rudy, Jr. et al. | |
| 5,688,229 A | 11/1997 | Bauer | |
| 6,090,058 A | 7/2000 | Traut et al. | |
| 6,245,033 B1 | 6/2001 | Martin | |
| 6,254,560 B1 | 7/2001 | Tweardy et al. | |
| 6,267,741 B1* | 7/2001 | Lerman | A61F 5/055 602/18 |
| 6,423,020 B1 | 7/2002 | Koledin | |
| 6,494,854 B1 | 12/2002 | Visness et al. | |
| 6,663,581 B1 | 12/2003 | Calabrese | |
| 6,872,188 B2 | 3/2005 | Caille et al. | |
| 7,041,073 B1 | 5/2006 | Patron | |
| 7,442,176 B2* | 10/2008 | Cojbasic | A61F 5/055 602/18 |
| 7,674,234 B2 | 3/2010 | Calco et al. | |
| 7,981,068 B2 | 7/2011 | Thorgilsdottir et al. | |
| 8,449,485 B2 | 5/2013 | Modglin | |
| 8,679,044 B2 | 3/2014 | Thorgilsdottir et al. | |
| 8,721,576 B2 | 5/2014 | Modglin | |
| 8,740,830 B2 | 6/2014 | Suarez et al. | |
| 8,858,481 B2 | 10/2014 | Thorgilsdottir et al. | |
| 8,864,693 B2 | 10/2014 | Suarez et al. | |
| 8,932,243 B2 | 1/2015 | Calabrese | |
| 9,011,357 B2 | 4/2015 | Modglin | |
| 9,132,027 B2 | 9/2015 | Calco | |
| 9,414,956 B2 | 8/2016 | Garth et al. | |
| 9,421,119 B2 | 8/2016 | Suarez et al. | |
| 9,668,906 B2 | 6/2017 | Thorgilsdottir et al. | |
| 9,713,546 B2 | 7/2017 | Thorsteinsdottir et al. | |
| 9,717,621 B2 | 8/2017 | Haider et al. | |
| 9,913,746 B2 | 3/2018 | Martin et al. | |
| 9,943,433 B2 | 4/2018 | Modglin | |
| 2002/0173737 A1* | 11/2002 | Miyaji | A61F 5/055 602/18 |
| 2003/0055367 A1* | 3/2003 | Dominguez | A61F 5/055 602/18 |
| 2003/0060744 A1 | 3/2003 | Caille et al. | |
| 2004/0176713 A1 | 9/2004 | Garth et al. | |
| 2007/0270728 A1 | 11/2007 | Chao | |
| 2010/0087764 A1* | 4/2010 | Linares | A61F 5/055 602/18 |
| 2010/0185130 A1 | 7/2010 | Patron | |
| 2010/0298748 A1 | 11/2010 | Rosenfeld et al. | |
| 2011/0034844 A1 | 2/2011 | Thorgilsdottir et al. | |
| 2011/0172579 A1 | 7/2011 | Chiu et al. | |
| 2012/0053499 A1 | 3/2012 | Donaldson et al. | |
| 2013/0261519 A1 | 10/2013 | Garth et al. | |
| 2014/0243720 A1 | 8/2014 | Modlin | |
| 2014/0323938 A1 | 10/2014 | Suarez et al. | |
| 2015/0133840 A1 | 5/2015 | Calabrese | |
| 2015/0150711 A1 | 6/2015 | Ven et al. | |
| 2016/0008158 A1 | 1/2016 | Martin et al. | |
| 2016/0058601 A1 | 3/2016 | Garth et al. | |
| 2016/0158054 A1 | 6/2016 | Calco | |
| 2016/0287424 A1 | 10/2016 | Webster et al. | |
| 2017/0136704 A1 | 5/2017 | Giulietti et al. | |
| 2017/0246022 A1 | 8/2017 | Calco et al. | |
| 2017/0252198 A1 | 9/2017 | Thorsteinsdottir et al. | |
| 2017/0266028 A1 | 9/2017 | Thorgilsdottir et al. | |
| 2017/0290695 A1 | 10/2017 | Haider et al. | |
| 2018/0000625 A1 | 1/2018 | Wang | |
| 2018/0028344 A1 | 2/2018 | Kim | |
| 2018/0042756 A1 | 2/2018 | Ahn | |
| 2018/0078400 A1 | 3/2018 | Hsu et al. | |
| 2018/0140455 A1 | 5/2018 | Chao | |

FOREIGN PATENT DOCUMENTS

| | | |
|---|---|---|
| WO | 9843568 A1 | 10/1998 |
| WO | 2006079284 A1 | 8/2006 |
| WO | 2013117069 A1 | 8/2013 |
| WO | 2016123408 A1 | 8/2016 |
| WO | 2017039699 A1 | 3/2017 |
| WO | 2017219220 A1 | 12/2017 |

OTHER PUBLICATIONS

U.S. Appl. No. 62/850,984, filed May 21, 2019, Alexis Doty.
U.S. Appl. No. 62/851,023, filed May 21, 2019, Alexis Doty.
U.S. Appl. No. 62/851,028, filed May 21, 2019, Alexis Doty.
International Search Report in PCT/US2020/033753 dated Sep. 30, 2020.

* cited by examiner

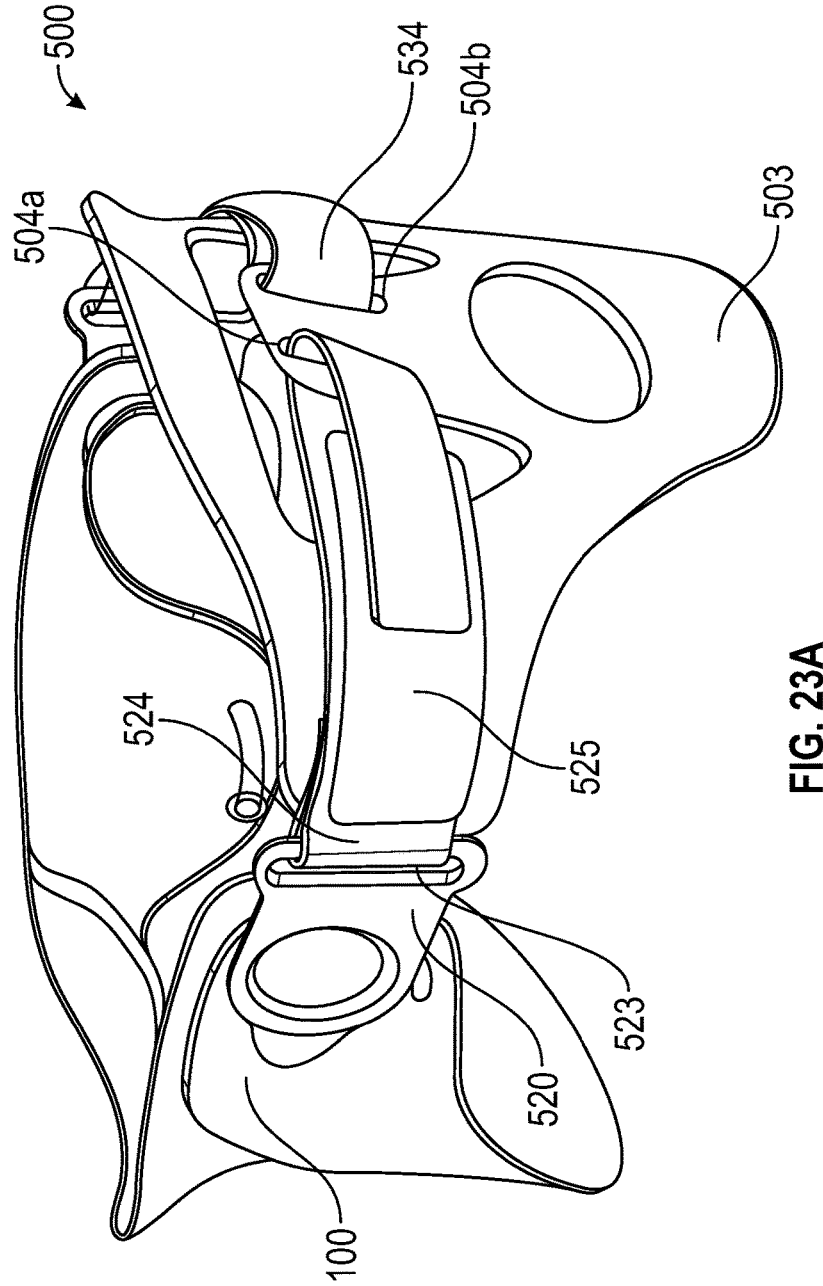
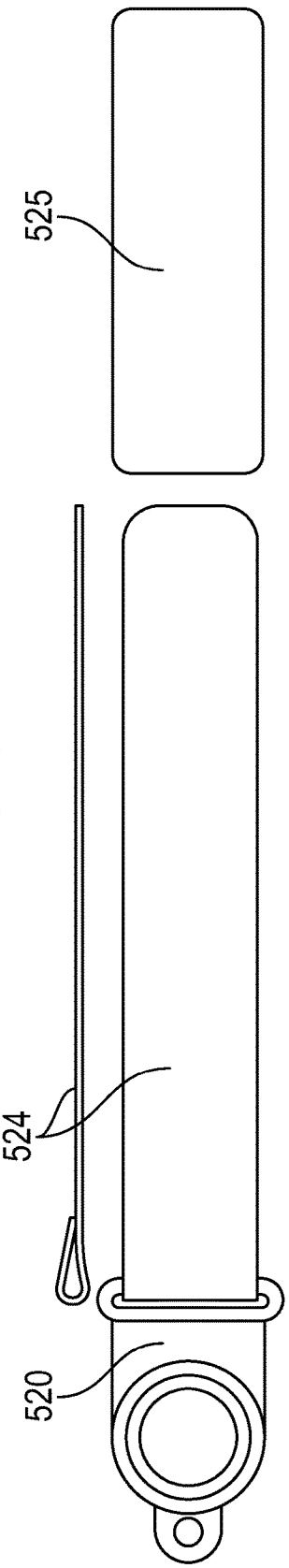
FIG. 23A
FIG. 23B

Conventional Pivot Point Angle

HEIGHT, DEPTH AND CIRCUMFERENTIAL ADJUSTMENT MECHANISMS FOR CERVICAL COLLAR

RELATED APPLICATIONS

This application claims priority to U.S. Provisional Application Nos. 62/850,958; 62/851,023; 62/851,028; 62/850,984; and 62/850,971, each of which was filed on May 21, 2019 and U.S. Provisional Application No. 62/872,510, filed on Jul. 10, 2019, U.S. Provisional Application No. 62/939,496, filed on Nov. 22, 2019, and U.S. Provisional Application No. 62/991,374 filed on Mar. 18, 2020. The entire contents of the aforementioned applications are hereby incorporated by reference.

FIELD OF THE INVENTION

The field of the invention relates to cervical collars.

BACKGROUND

Cervical collars are generally used to maintain a spine in neutral alignment. To maintain neutral alignment, the user's chin must be supported at a particular position. Thus, conventional cervical collars generally have a chin piece that supports the chin of a wearer and collar body that rests upon the trapezius muscles.

U.S. Pat. No. 7,674,234, which is incorporated herein by reference, relates to a cervical collar having a chin piece, a collar body, and a chin height adjustment mechanism comprising a first rack that cooperates with a pinion, disposed such that a single adjustment to the adjustment mechanism operates to raise both lateral sides of the chin piece relative to the collar body. U.S. Pat. No. 7,674,234 states that:

> the terms "rack" and "pinion" are used herein in a broader manner than ordinary usage, and include embodiments with teeth of any size, or indeed no teeth at all. In the latter case, for example, the rack and pinion can each have rubbery surface that together provide sufficient friction to couple the relatively motions [sic] of the rack and pinion. Moreover, in common usage one often refers to the rack portion of a rack and pinion as being flat. As used in this application, a rack need not be flat, and indeed in most instances will be curved. The only essential feature of the racks and pinions as used herein is that the rack translates in space as the pinion rotates. Where discussion is limited to a toothed rack and pinion, either the teeth are expressly stated, or the pinion is referred to as a pinion gear.

Medical professionals who are tasked with fitting many different sized patients per day with cervical collars, have voiced complaints that conventional cervical collars with a single height adjustment mechanism are difficult and time consuming to operate, causing finger pain after fitting many patients, which prevents them from comfortably fitting patients.

Further, some conventional cervical collars having a pivot point and provide a camming rotation that retracts the chin portion back into the coronal plane of the body and thus limits properly fitting collars to fewer users. Retraction of the chin portion back into the coronal plane of the body commonly occurs with conventional collars that comprise conventional pivot systems between the chin portion and the body portion, which may be able to surpass an acute angle when fitted to a patient.

Conventional cervical collars generally comprise a posterior component that may have hook and loop straps on either ends, which are connected to the anterior component and individually adjusted to accommodate various circumferences of patients' necks. Patients who remove the cervical collar, for example to bathe, often are unable to repeat the same proper fitting as provided by medical professionals and often use trial and error by detaching and reattaching the straps in an attempt to evenly align the anterior and posterior components. Thus, a medical professional's fitting is unable to be consistently repeated by the user causing inferior results.

In addition, conventional collars typically do not allow an adjustment of the chin piece to account for the depth of a user's chin, causing the cervical collar to fit few patients or fit patients improperly.

SUMMARY OF THE INVENTION

To overcome these and other disadvantages of conventional cervical collars, a cervical collar and components thereof are provided wherein a single adjustment to a height adjustment mechanism operates to bilaterally adjust the height of the space between an upper and lower portion of an anterior cervical collar component to accommodate patients' various length necks. Typically, during a fitting, a single adjustment to the adjustment mechanism can be made comfortably by a medical professional, causing the upper and lower portions to be raised and positioned to accommodate the particular neck length of a patient.

Using the height adjustment mechanisms herein, the height of the space between a chin portion and a body portion of an anterior cervical collar may be elongated in a substantially vertical direction, that is, substantially parallel to the coronal plane and perpendicular to the transverse plane of the body. Thus, the cervical collars having the anterior portions herein allow the chin portion to rise substantially vertically and thereby increasing the fit range of more users. The height adjustment mechanism herein allows the collar to maintain an acute angle between the chin portion and the body portion when the height adjustment is made, as shown in FIG. 30b. In comparison to conventional pivot systems (FIG. 30a), the chin portion and a body portion of a conventional anterior cervical collar may surpass an acute angle when the height is adjusted.

In addition, to overcome these and other disadvantages of conventional cervical collars, a chin piece is provided that may be adjusted to accommodate the depth of a patient's neck.

Further, to overcome these and other disadvantages of conventional cervical collars, a cervical collar with circumferential adjustment mechanism is provided that can be fitted by medical professionals and retains the circumferential dimensions upon redonning after removal by a patient. Various strap systems, circumferential sizing and adjusting mechanisms, mating pieces, or a cam surface assembly herein can overcome disadvantages of conventional circumferential adjustment mechanisms.

In some embodiments, regarding the height adjustment mechanism, an anterior component of a cervical collar may have a chin portion and a body portion, comprising a height adjustment mechanism wherein a single adjustment of the adjustment mechanism raises and lowers lateral sides of the chin portion relative to the body portion, wherein the adjustment mechanism raises and lowers the chin portion substantially vertically.

In some embodiments, the height adjustment mechanism does not comprise a rack that cooperates with a pinion; or a cable and/or a pulley; wherein the chin portion and the body portion are not pivotally coupled and are not supported only on ends of the chin portion and the body portion respectively; and wherein the chin portion is unable to bend to fit a user's chin contours when in use.

In particular, in some aspects, the height adjustment mechanism may comprise a four bar adjustment mechanism. In some aspects, the four bar adjustment mechanism may comprise a pair of cross bars positioned laterally on either side of the anterior component between a chin portion and a body portion thereof. The four bar adjustment mechanism may comprise a pair of lead screws positioned laterally on either side of the anterior component; wherein the lead screws are each rotatably coupled to shuttles; wherein each of the shuttles is coupled to an actuator bar on a first end; wherein each actuator bar is coupled on a second end to a first end of a single first cross bar of each of the cross bars; wherein an end of each pair of lead screws may comprise a bevel gear that engages a drive gear.

In some aspects, the chin portion may comprise a first and second lateral chin portion each defining an elongate slot therein; wherein the body portion may comprise a first and second lateral body portion each defining an elongate slot therein; wherein the coupled second end of each actuator bar is configured to ride in the elongate slot in each of the first and second lateral body portion; wherein a first end of a single second cross bar of each of the cross bars is configured to ride in the elongate slot in each of the first and second lateral chin portion; wherein a second end of the single second cross bar of each of the cross bars is rotatably coupled in a stationary position to each of the first and second lateral body portion; wherein a second end of the single first cross bar of each of the cross bars is rotatably coupled in a stationary position to each of the first and second lateral chin portion.

In some aspects, the height adjustment mechanism may comprise a lead screw that cooperates with a lead screw nut or shuttle or a latching mechanism, in addition to or separate from the four bar adjustment mechanism.

In any of the embodiments herein an anterior component of a cervical collar may comprise a one-piece cervical collar shell comprising a chin portion, a body portion, and a deforming portion therebetween. The one-piece cervical collar shell may comprise elongate slots therein. In some aspects, the chin portion and the body portion have a deforming portion therebetween and form a one-piece cervical collar shell. The chin portion and body portion may comprise a springing mechanism therebetween that may be biased to open to an acute angle between the chin portion and the body portion.

In some aspects, a chin portion, a body portion, a spring mechanism, and latching mechanism are disposed such that a single adjustment of the latching mechanism raises the lateral sides of the chin portion relative to the body portion. The spring mechanism between the chin portion and the body portion may be biased to open to an acute angle between the chin portion and the body portion, and can be closed to a relatively smaller acute angle. In some aspects, the spring mechanism is a deforming portion of a one-piece cervical collar shell.

In some aspects, the body portion may comprise indicia indicating the height of the chin portion.

In some aspects, the anterior component may comprise a pair of lateral chin portions moveably coupled to a chin rest therebetween.

In some aspects, the anterior component may comprise a chin depth adjustment mechanism. The chin depth adjustment mechanism may provide substantially horizontal movement of the chin piece with respect to the pair of lateral chin portions when oriented in the same position as if under a chin of an upright user, i.e., may provide movement in a substantially horizontal direction that is perpendicular to the coronal plane and parallel to the transverse plane of the body. The chin depth adjustment mechanism may comprise a substantially horizontal depth adjustment slot for receiving a coupler that slides horizontally within the substantially horizontal depth adjustment slot. The pair of lateral chin portions may each comprise the substantially horizontal depth adjustment slot that accepts a coupler, such as a rivet, positioned on each end of the chin rest. In some aspects the chin rest pivots.

In some aspects, the cervical collar herein may comprise a circumferential adjustment mechanism. The posterior component may comprise a strap having sizing indicia and a back panel; wherein the strap has a first end and a second end; wherein sizing indicia may be positioned between the first end and the second end; wherein the strap has an alignment indicium proximate the first end; wherein the strap may have removably coupled to the anterior component; and wherein an alignment of the alignment indicium proximate the first end of the strap corresponds with the alignment indicium on the body portion. The second end of the strap may be removably coupled to the back panel and may be coupleable to itself. In some aspects, the alignment of an edge of the second end of the strap corresponds to one of the sizing indicia upon coupling to itself.

Other circumferential adjustment mechanisms are also contemplated, for example, a cam surface assembly component. A cam surface assembly may be coupleable to a strap; disposed such that the strap may be adjusted to a length that fits a patient's neck circumference when donning a cervical collar, and disposed such that the cam surface assembly may be removed from a cervical collar without disturbing said strap having said length.

In some aspects, the posterior component may comprise the cam surface assembly, which may be removably coupled thereto. In some aspects, the anterior component may comprise the cam surface assembly. In some aspects, the cam surface assembly is coupleable to a strap attached thereto. The cam surface assembly may be removed from the anterior component without disturbing a length of the strap. For example, a cervical collar may comprise an anterior component; a posterior component comprising a back panel and a strap; and a cam surface assembly coupleable to the anterior component and posterior component; disposed such that the strap may be adjusted to a length that fits a patient's neck circumference, and disposed such that the cam surface assembly may be removed from the cervical collar without disturbing said strap having said length.

In some aspects, a circumferential adjustment mechanisms may comprise a posterior component of a cervical collar having a back panel comprising a posterior mating piece having a coupler proximate a first end and a strap proximate a second end; wherein the strap is coupled to the back panel; disposed such that the strap may be adjusted to a length that fits a patient's neck circumference, and disposed such that the posterior mating piece may be removed from a cervical collar without disturbing said strap having said length. The posterior component may further comprise an anterior mating piece for receiving the posterior mating piece. In some aspects, the posterior mating piece may be removably coupled to the back panel. In some aspects, the strap may be permanently attached to the posterior mating piece.

In some aspects, the cervical collar or portion thereof does not include a rack and pinion.

Methods include adjusting the height adjustment mechanism to fit the length of a user's neck, adjusting the circumferential adjustment mechanism to fit the circumference of a user's neck, adjusting the chin depth adjustment mechanism to fit the depth of a user's chin, donning and/or redonning the collar while reproducibly maintaining predetermined adjustments, and/or combinations thereof.

Other features and advantages will be apparent from the following detailed description, the drawings, and the claims.

BRIEF DESCRIPTION OF THE DRAWINGS

FIG. 23a is a perspective view of an embodiment of an adjustable posterior component of a cervical collar attached to an anterior component. FIG. 23b is a line depiction of the adjustable straps.

DETAILED DESCRIPTION

Figure 1:
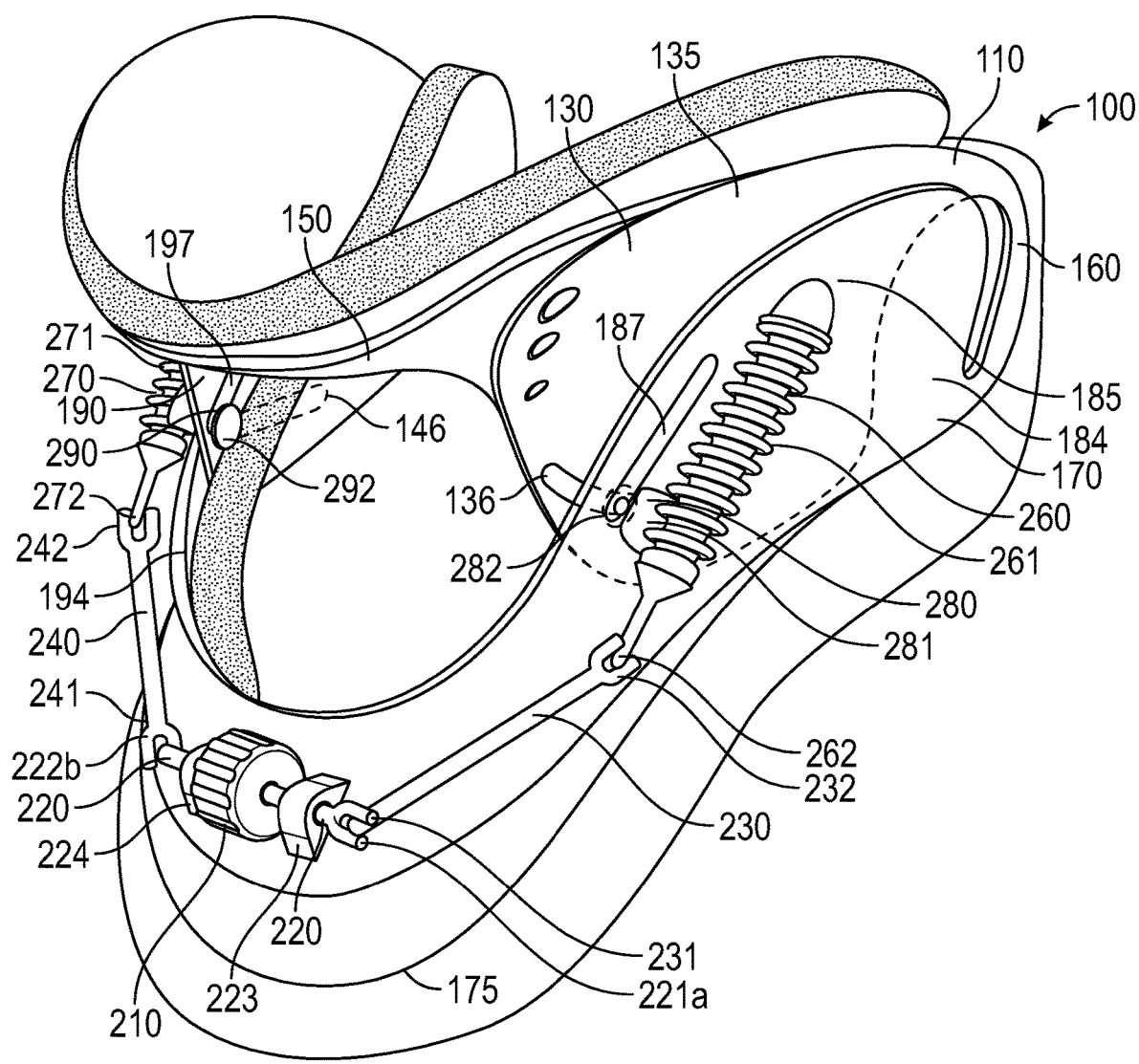
FIG. 1 is a front perspective view of an embodiment of an adjustable anterior component of a cervical collar cervical collar in a position before an adjustment is made to raise the height.

The term "anterior" has its ordinary meaning and refers to a location ahead of or to the front of another location. The term "posterior" also has its ordinary meaning and refers to a location that is behind or to the rear of another location.

In reference to FIGS. 1-5, 9-10, and 13-14, embodiments herein provide an adjustable anterior component 100 of a cervical collar comprising a height adjustment mechanism 200 that can simultaneously raise and lower lateral chin portions 135, 145 or lateral body portions 184, 194 of the anterior component 100, depending on which portion is held in a fixed position, with a single motion, such as by adjusting a sliding actuator 210, adjusting a spring and latch mechanism, or turning a knob. A single motion refers to the ability to simultaneously raise and/or lower lateral chin portions 135, 145 and/or lateral body portions 184, 194 of the anterior component 100, without adjusting the height of each lateral portion of the cervical collar separately. Herein, the single motion may refer to the chin portion being raised or lowered, which assumes the body portion is held in a fixed position as it would be if the body portion was held near a user's body during a fitting.

In addition to the sliding actuator, spring and latch mechanism, or knob, the height adjustment mechanism 200 may further comprise, for example, a lead screw, four bar height adjustment mechanism, additional bars, or components that overcome the disadvantages of a conventional cervical collar having a pivot mechanism, cable mechanism, or rack and pinion mechanism, such as disclosed in U.S. Pat. Nos. 7,674,234, 8,864,693, 8,740,830, 9,421,119, 8,449,485, 8,721,576, 9,943,433, 9,011,357, 9,132,027, 9,713,546, 9,913,746, 9,717,621 and US Pat. Publ. Nos. 20160287424A1, US20180140455A1, and US20180078400A1.

In some embodiments, the first lateral body portion 184 and/or the second lateral body portion 194 may have a first height adjustment indicia 186 and/or a second height adjustment indicia 196 (not shown) respectively. (FIGS. 18, 25) One or both height adjustment indicia 186, 196 may align with corresponding indicia (not shown) on a first lateral chin portion 135 and/or a second lateral chin portion 145. The corresponding indicia (not shown), may be a marking, such as a polished lower edge, on the first lateral chin portion 135 and/or the second lateral chin portion 145 that corresponds to the height adjustment indicia 186, 196. Thus, once the height of the chin portion 130 relative to the body portion 170 is prescribed by a medical professional based on an individual patient's anatomy, a medical professional who fits the collar to the patient, or the patient, can adjust the height to the prescribed height. The prescribed height may be locked in position as discussed below in more detail to prevent the patient from possibly making an inaccurate adjustment when donning and redonning the collar.

Instead of a separate chin portion 130 and a body portion 170, also contemplated is a one-piece shell 110 as shown in FIGS. 1-5 that may comprise a chin portion 130, a body portion 170, deforming portions 160, 161 that are integral with the one-piece shell 110 and proximate the portion of the one-piece shell 110 where the chin portion 130 meets the body portion 170. In some aspects, the chin portion 130 may comprise a pair of lateral chin portions 135, 145 with a chin rest 150 therebetween, for resting the chin of a user. The body portion 170 may have lateral body portions 184, 194 that meet at a central portion 175. In some aspects, the one-piece shell does not comprise the height adjustment mechanism.

Figure 2:
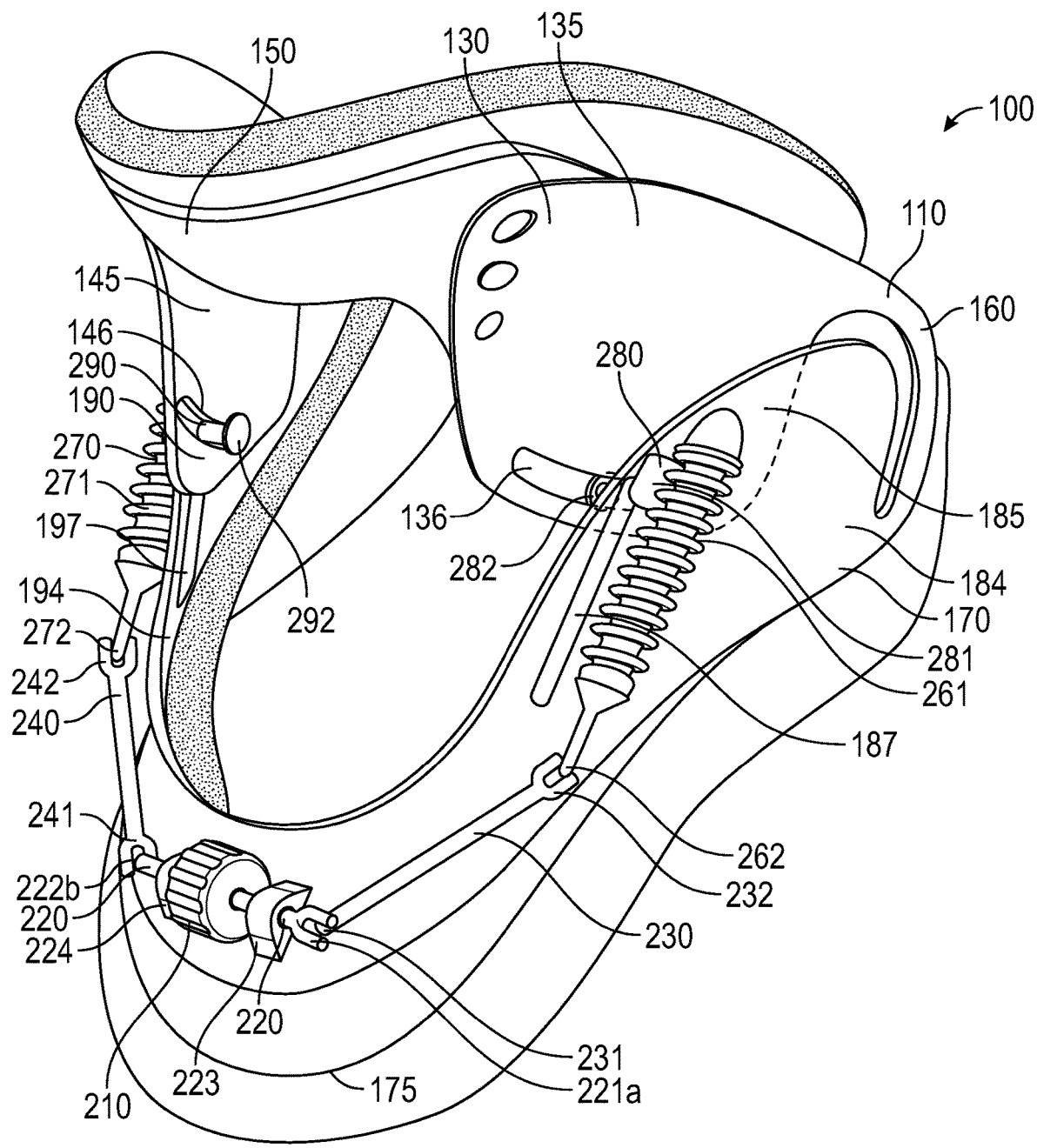
FIG. 2 is a front perspective view of an embodiment of an adjustable anterior component of a cervical collar in a position after an adjustment is made to increase the height of the chin portion relative to the body portion.
Figure 3:
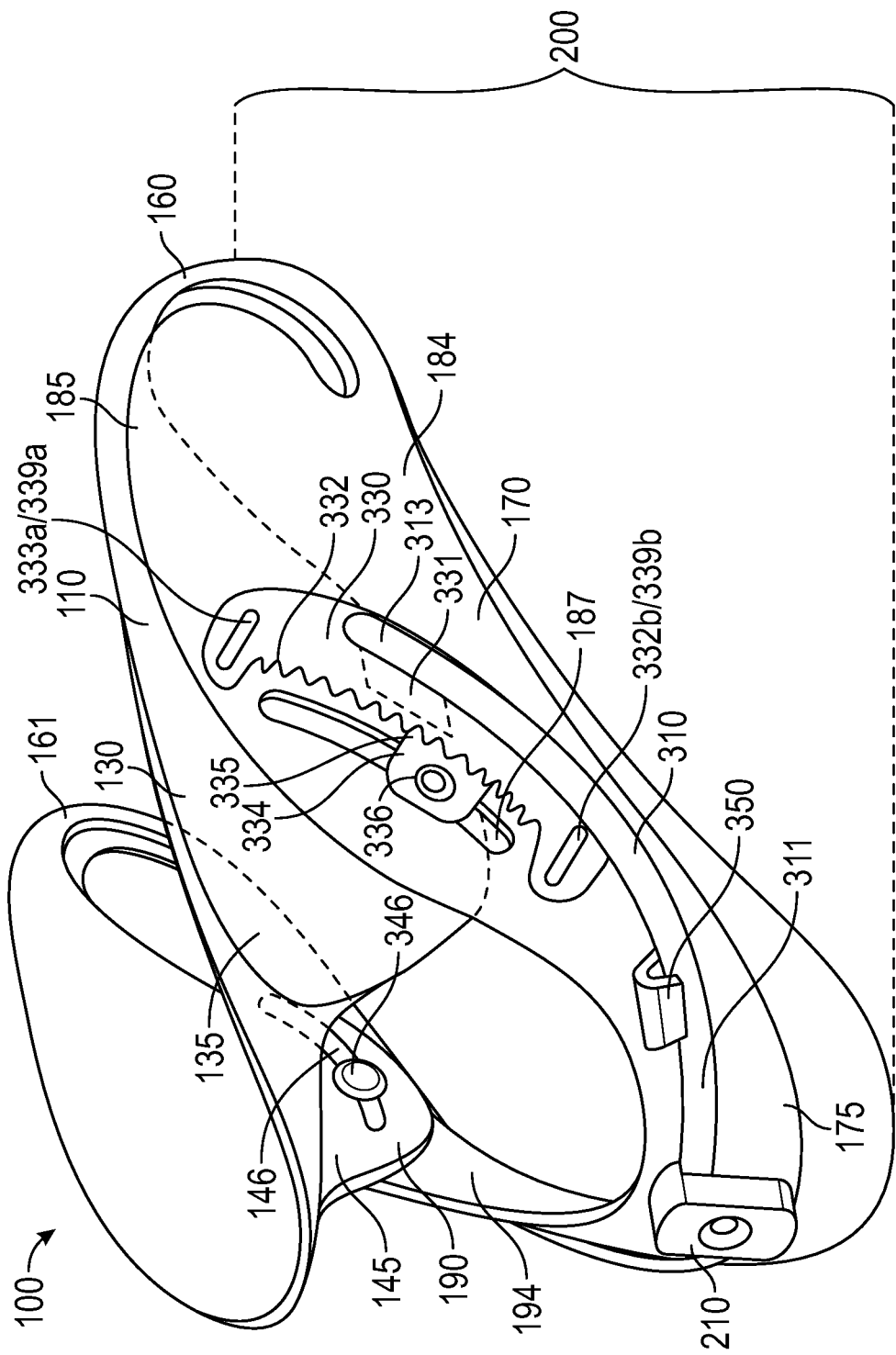
FIG. 3 is a front perspective view of an embodiment of an adjustable anterior component of a cervical collar in a latched position before an adjustment is made.
Figure 4:
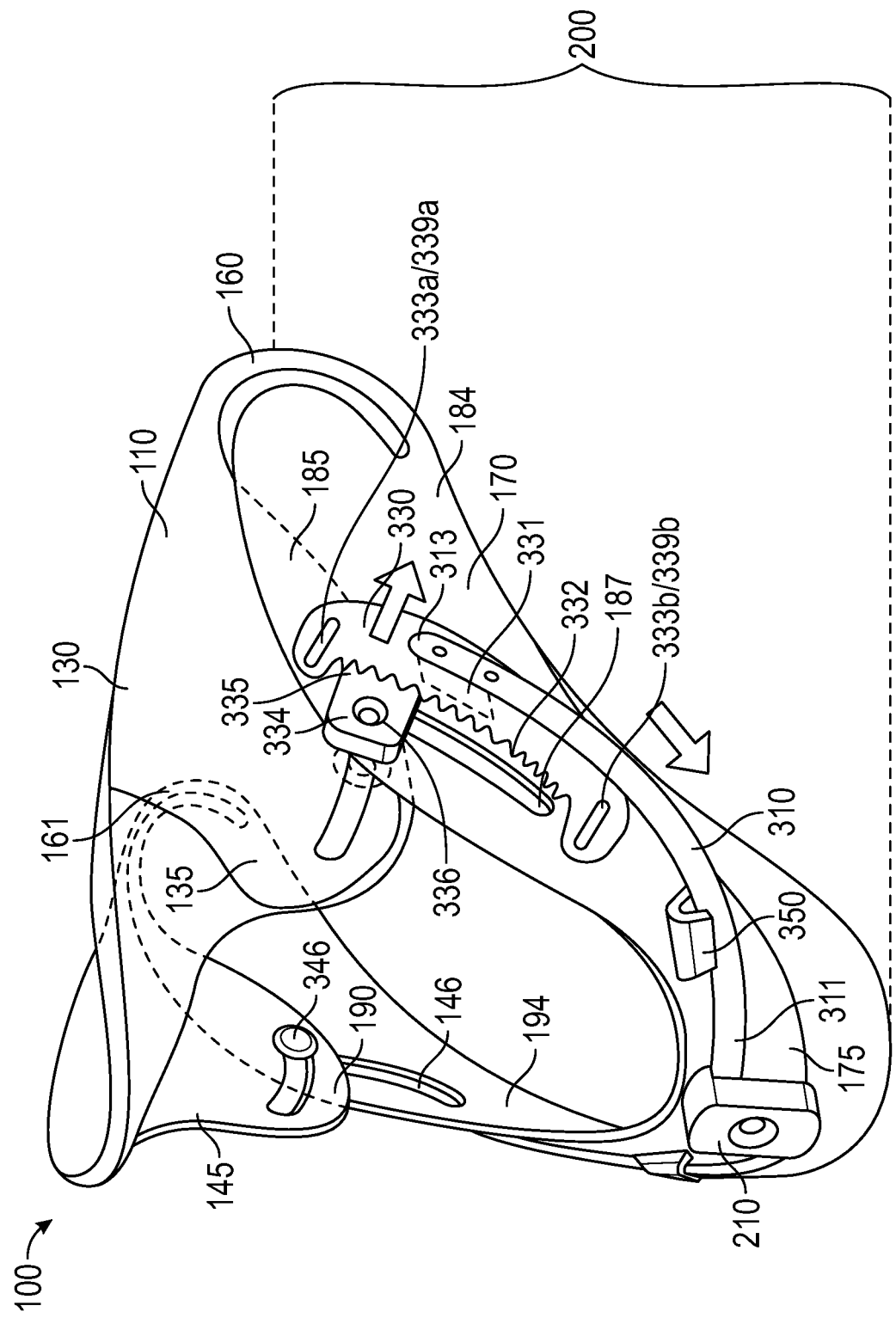
FIG. 4 is a front perspective view of an embodiment of an adjustable anterior component of a cervical collar in a latched position after an adjustment is made to increase the height of the chin portion relative to the body portion.
Figure 5:
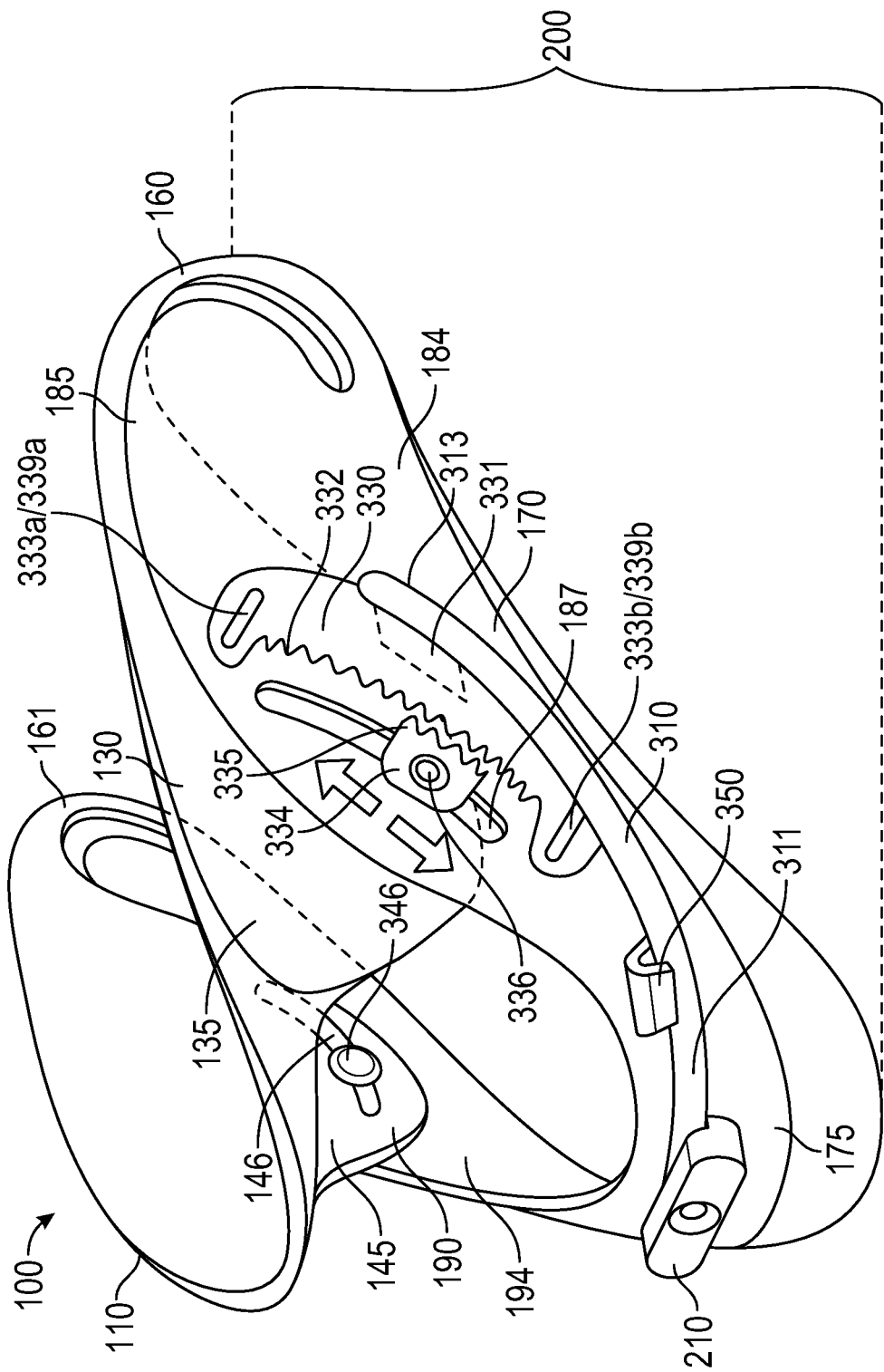
FIG. 5 is a front perspective view of an embodiment of an adjustable anterior component of a cervical collar in an unlatched position.
Figure 29:
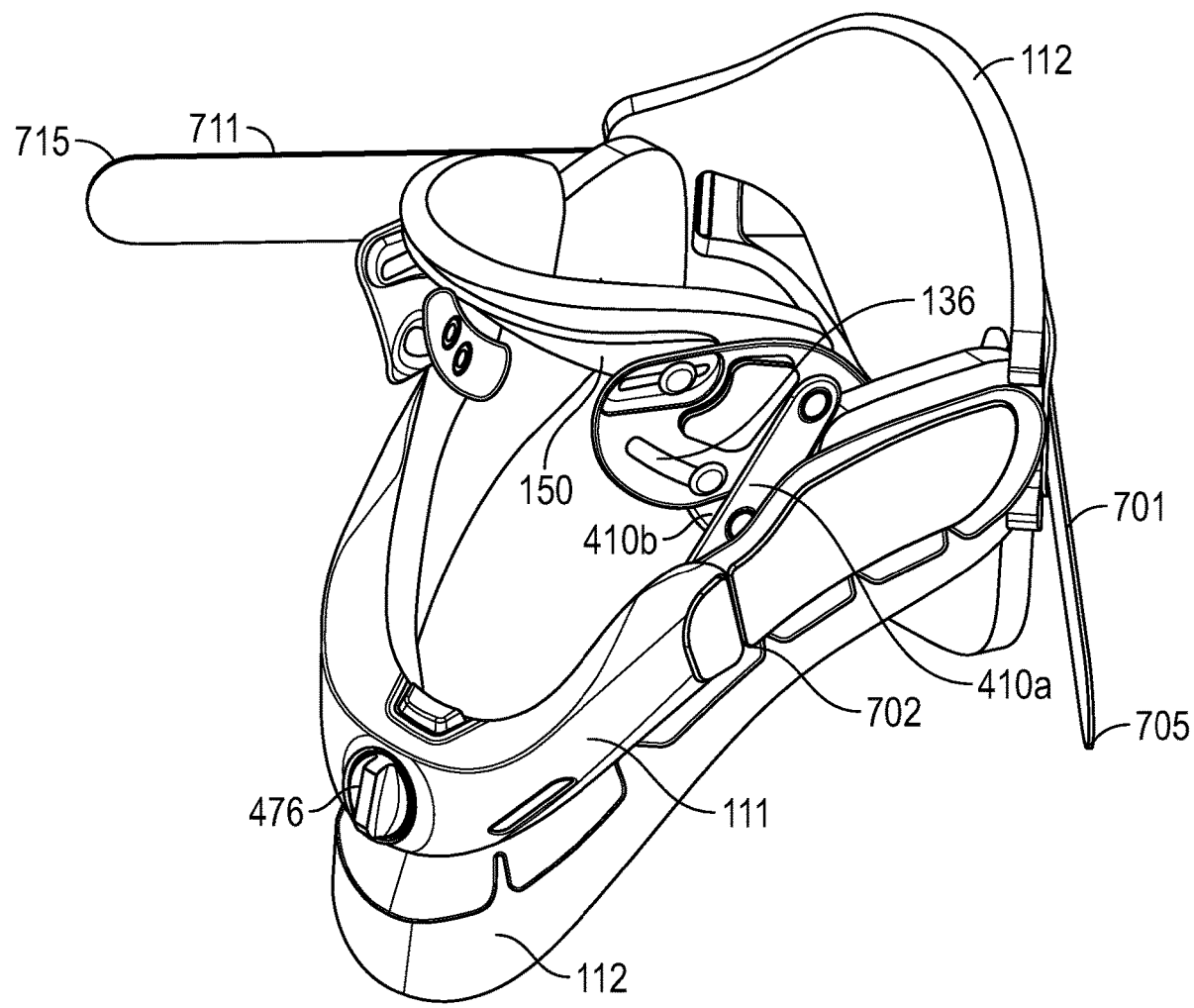
FIG. 29 is a perspective view of an embodiment of a cervical collar with both anterior and posterior components with foam padding coupled with straps open circumferentially.

Embodiments of an anterior component 100 of a cervical collar comprising a one-piece shell 110, mechanism enclosure 111 (e.g., FIG. 29), and height adjustment mechanism 200 are illustrated, for example, in the lead screw assembly FIGS. 1-2 or a latching mechanism FIGS. 3-8.

In some aspects, when deformed as part of the anterior component, a first lateral chin portion 135 may overlap a first lateral body portion 184. At the same time, a second lateral chin portion 145 may overlap second lateral body portion 194. Parts of the adjustment mechanism that as a whole move the chin portion 130 relative to the body portion 170 may be found proximate to this overlapping area, i.e., first upper overlap portion 180 (obscured border shown as dashed lines), second upper overlap portion 190, first lower overlap portion 185 and second lower overlap portion 195 (not shown). The size of the overlapping area varies and depends on the setting to which the adjustment mechanism is adjusted. An overlapping portion may be shown in part by the boundary of the dotted line from the lower first lateral chin portion 135 and the upper edge of the first lateral body portion 184, for example, as illustrated in e.g., FIGS. 1-5.

The deforming portions 160, 161 provide a spring action such that when coupled to a height adjustment mechanism 200, the medical professional who fits the cervical collar will be able to more easily move the chin portion 130 away from the body portion 170. Deforming portions 160, 161 maybe integral with the one-piece shell 110, although separate or different springs are also contemplated such as torsion springs, leaf springs, compression springs, pneumatic springs, expansion springs, magnetic springs or springs, such as those made from radiolucent material. Although non radiolucent materials such as metal springs are contemplated, they are not ideal when X-rays, CAT scans or PET scans are needed as spinal injuries may preclude removing a cervical collar to perform scan.

In addition, slowing elements may be incorporated to slow the spring speed of the deforming body when the knob is opened to provide a more controlled lift.

In some aspects, a one-piece shell 110 having deforming portions 160, 161 herein (e.g., FIGS. 1-5) has mechanical advantages over a pivot when used in the context of a cervical collar. A pivot connecting two lateral arms, for example, may be rotatable and lack tension to hold an angle between the two parts. A cervical collar may need to provide an additional lift mechanism to compensate for the lack of tension, which may be omitted in the present embodiments. If the pivot point is tightened to provide more tension to hold an angle, undesirable friction between the lateral arms upon pivoting may interfere with the smooth operation of the cervical collar. An anterior component with deforming portions 160, 161 as recited herein overcomes these disadvantages. Further, the deforming mechanism contains fewer individual parts, which provides a more robust mechanism because it has fewer points of failure.

In addition to the height adjustment mechanisms herein, the one-piece shell 110 can be used with other adjustment mechanisms, such as a rack and pinion and/or cable adjustment mechanisms.

In one embodiment, the height adjustment mechanism may comprise a lead screw that may be operated in conjunction with a lead screw nut. Other similar mechanisms are also contemplated. For example, a threadless mechanism may operate like a lead screw and nut, however the operation may be based on an angled rod and bearings, wherein the rod may be similarly rotated and moves linearly when operated in conjunction with the bearings using friction.

In some aspects, the lead screw nut may provide a greater contact area on the lead screw, in comparison to the contact area of a conventional rack and pinion system, and has fewer parts. This greater contact area between lead screw and the lead screw nut provides a greater mechanical advantage in comparison to conventional mechanisms such as rack and pinion mechanisms or cable systems. The lead screw mechanism when coupled to a cervical collar body allows for a large adjustment input that creates a small output for more precise fine adjustment to raise and lower the chin portion. Further, the lead screw mechanism allows a greater load in comparison to a rack and pinion system so more weight can be exerted on the chin portion providing additional mechanical advantages. Thus, these mechanical advantages over other cervical collars allow medical professionals' problems associated with fitting multiple patients with cervical collars to be avoided. The lead screw mechanism may be used on any conventional collar body. Additional advantages are apparent when used with the one-piece shell provided herein.

Referring to FIGS. 1-2, an embodiment of an anterior component 100 of a cervical collar may comprise a one-piece shell 110, mechanism enclosure (not shown) 111, and a lead screw assembly (height adjustment mechanism 200).

In some aspects, proximate the overlapping area (approximate boundary of the portions that overlap within the dotted line in FIGS. 1-2), a first lateral chin portion 135 has a first chin elongate slot 136 for receiving a first lead screw nut 280. Similarly, a second lateral chin portion 145 has a second chin elongate slot 146 for receiving a second lead screw nut 290.

The first lead screw nut 280 has a first female end 281 positioned proximate the outside surface of the first lower overlap portion 185 that cooperates with first male threads 261 of a first lead screw 260. Spaced from the first female end 281 may be a first terminal end 282 that may be positioned proximate an outside surface of the first upper overlap portion 180.

Similarly, the second lead screw nut 290 has a second female end 291 (not shown) positioned proximate the outside surface of second lower overlap portion 195 (not shown) that cooperates with second male threads 271 of a second lead screw 270 and a second terminal end 292 spaced from the second female end 291 that may be positioned proximate an outside surface of the second upper overlap portion 190. Components herein on the second side may be obscured in the figures and generally correspond to the first side components.

The first lateral body portion 184 may be connected to a first lead screw 260 on a first lower overlap portion 185 for cooperating with a first lead screw nut 280; and a second lateral body portion 194 may be connected to a second lead screw 270 on a second lower overlap portion 195 for cooperating with a second lead screw nut 290.

The first lateral body portion 184 has a first body elongate slot 187 on a first lower overlap portion 185 for receiving the first lead screw nut 280; and a second lateral body portion 194, having a second body elongate slot 197 on a second lower overlap portion 195 for receiving a second lead screw nut 290.

In some aspects, lead screws 260, 270 may be attached to the body portion 170 using bushings 263a, 263b, 273a, 273b (not shown) on either end, which include connectors that can attach the lead screws 260, 270 to the body portion 170 while retaining the function of the lead screw. The bushings may be a separate component or may be integral with the lateral body portions 184, 194.

In some aspects, for example when in use as part of a cervical collar, the chin elongate slots 136, 146 partially overlap the body elongate slots 187, 197 respectively, so that a path may be defined along which lead screw nuts 280, 290 travel when respectively cooperating with lead screws 260, 270 that will allow the chin portion 130 to be raised or lowered in relation to the body portion 170 to conform to the neck length and anatomy of an individual patient, when adjusted using a height adjustment mechanism 200.

In some aspects, the body portion 170 may be connected to a height adjustment mechanism 200 for raising and lowering the first lateral chin portion 135 and second lateral chin portion 145 simultaneously.

In some aspects, the height adjustment mechanism 200 may comprise an adjustment knob 210 in the central portion 175 of body portion 170 that may be engaged with a drive shaft 220. The drive shaft 220 may terminate in a first flexible joint 221a and a second flexible joint 222a, such as a U-joint. The first flexible joint 221a may be moveably coupled to a first proximal end 231 of a first lateral drive shaft 230 and a second flexible joint 222b moveably coupled to a second proximal end 241 of a second lateral drive shaft 240.

A first distal end 232 of the first lateral drive shaft 230 may be moveably coupled to a first coupling end 262 of the first lead screw 260.

A second distal end 242 of the second lateral drive shaft 240 may be moveably coupled to a second coupling end 272 of the second lead screw 270.

In some aspects, the drive shaft portion 220 may comprise a first drive shaft support 223 and a second drive shaft support 224 (not shown) on one or either side of the adjustment knob 210.

Lead screw nuts 280, 290 may be nonlinear (curved or straight) pieces where the same surface area of a nut (female ends 281, 291) engages different portions of the rotating lead screws 260, 270. When in use, in some aspects, rotating the adjustment knob 210 simultaneously drives both lateral drive shafts 230, 240, which in turn drive respective lead screws 260, 270. The lead screws 260, 270 cooperate with the lead screw nuts 280, 290 which respectively engage elongate slots 136, 146 causing the upper overlap portions 180, 190 to travel along the path of the elongate slots 136, 146, which allows the chin portion 130 to travel away from the body portion 170 to increase the space between them, thus adjusting the height of the cervical collar.

In some aspects, the deforming portions 160, 161 comprise a region connecting the chin portion 130 to the body portion 170. The region may be sufficiently long and thin such that it allows otherwise rigid material to flex, thereby allowing the chin portion 130 and the body portion 170 to be moved relative to one another. In some aspects, the one-piece shell in a resting position has the chin portion 130 and the body portion 170 roughly at an acute angle, when no adjustment mechanism may be present or when not otherwise coupled to one another. "Roughly at an acute angle" serves as a comparison to conventional pivot systems that may be able to surpass an acute angle under similar configuration when a chin piece and collar body are not otherwise coupled to one another except for the pivot point. In some aspects, the spring biases the chin portion 130 and the body portion 170 away from each other to the longest height setting.

In some aspects, the spring, such as in accordance with the deforming portions 160, 161, allows the chin portion 130 to travel back and forth in space relative to the body portion 170. The height adjustment mechanism 200 controls the force of the bias which keeps the chin portion 130 away from the body portion 170. For example, the height adjustment mechanism 200 comprising, for example, the lead screws 260, 270 guides the extent of the springing and holds the chin portion 130 and the body portion 170 from springing farther than necessary to provide the appropriate distance between the chin and the trapezius muscles of a patient. Although the lead screw 260, 270, for example, can be used to shorten the distance between the chin portion 130 and the body portion 170 while conforming to the chin and the trapezius muscles of a patient, it would typically not be used to shorten the distance unless fine tuning. The chin portion 130 and the body portion 170 can be manually pushed together to as well to close the gap to assist, for example, the lead screws 260, 270.

In one embodiment, an adjustable anterior component of a cervical collar may comprise a latching mechanism, which overcomes the disadvantages of a conventional cervical collar recited herein. For example, the latching mechanism has fewer parts in comparison to the contact area of conventional mechanisms such as rack and pinion or cable system and has fewer parts. The latching mechanism when coupled to a cervical collar body takes advantage of the springing mechanism that biases the chin portion and the body portion away from each other. Thus, these mechanical advantages over other cervical collars allow medical professionals' problems associated with fitting multiple patients with cervical collars to be avoided. Additional advantages are apparent when used with the one-piece shell recited herein.

With regard to FIGS. 3-8 directed to a latching mechanism, many aspects of the one-piece shell 110 are similar to the lead screw assembly discussed above and the parts are similarly numbered, which are discussed below in more detail.

In some aspects, the body portion 170 may be connected to a latching mechanism (height adjustment mechanism 200) for raising the first lateral chin portion 135 and second lateral chin portion 145 simultaneously. Lowering the first lateral chin portion 135 and second lateral chin portion 145 simultaneously may be performed manually or by using a lowering mechanism.

With regard to FIGS. 3-8 in some aspects, the spring, such as in accordance with the deforming portions 160, 161, allows the chin portion 130 to travel in space relative to the body portion 170. The height adjustment mechanism 200 controls the force of the bias that keeps the chin portion 130 away from the body portion 170. For example, the height adjustment mechanism 200 comprising the latching mechanism guides the extent of the springing and holds the chin portion 130 and the body portion 170 from springing farther than necessary to provide the appropriate distance between the chin and the trapezius muscles of a patient. Although the latching mechanism can be used to shorten the distance between the chin portion 130 and the body portion 170 while conforming to the chin and the trapezius muscles of a patient, it would typically not be used to shorten the distance unless fine tuning the cervical collar. The chin portion 130 and the body portion 170 can be manually pushed together to as well to close the gap to assist in lowering the height.

In some aspects, the self-sizing latch mechanism takes advantage of a spring action of, for example, the deforming portions 160, 161 of the one-piece shell 110 as recited herein, and the height adjustment mechanism 200 may comprise an adjustment knob 210 that acts as a locking mechanism to adjust the height of the chin portion. In some aspects, the adjustment knob 210 may be positioned in the central portion 175 of body portion 170. Once the adjustment knob 210 releases the lock, the chin portion 130 opens away from the body portion 170, by releasing the springing force of the deforming portions 160, 161, and the cervical collar may be fitted to the appropriate size of the user. The height position may be set and locked in place by returning the adjustment knob 210 to the original position. Once the adjustment is made, the patient is not required to reset the size after removing and then redonning the cervical collar, which has advantageous repeatability in comparison to conventional collars, which might not be sized properly by the patient after removing and redonning. In addition, the self sizing height adjustment mechanism 200 contains fewer individual parts than a rack and pinion or cable mechanism, for example, which provide a more robust mechanism because it has fewer points of failure.

Figure 6:
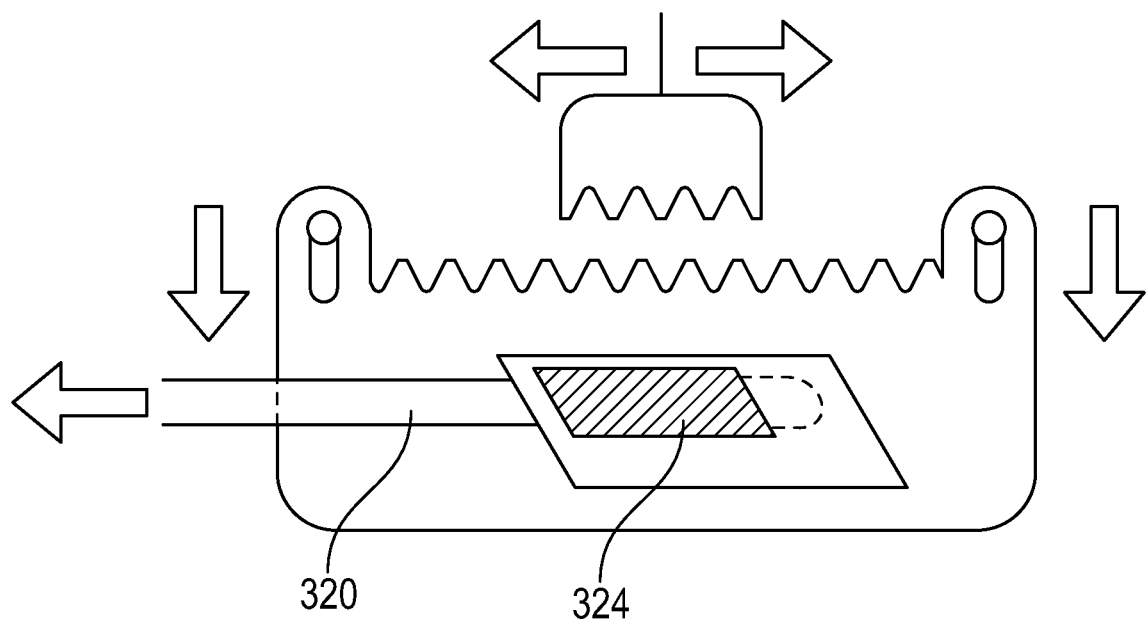
FIG. 6 is a side sectional view of an embodiment of the latching mechanism in the open position.
Figure 7:
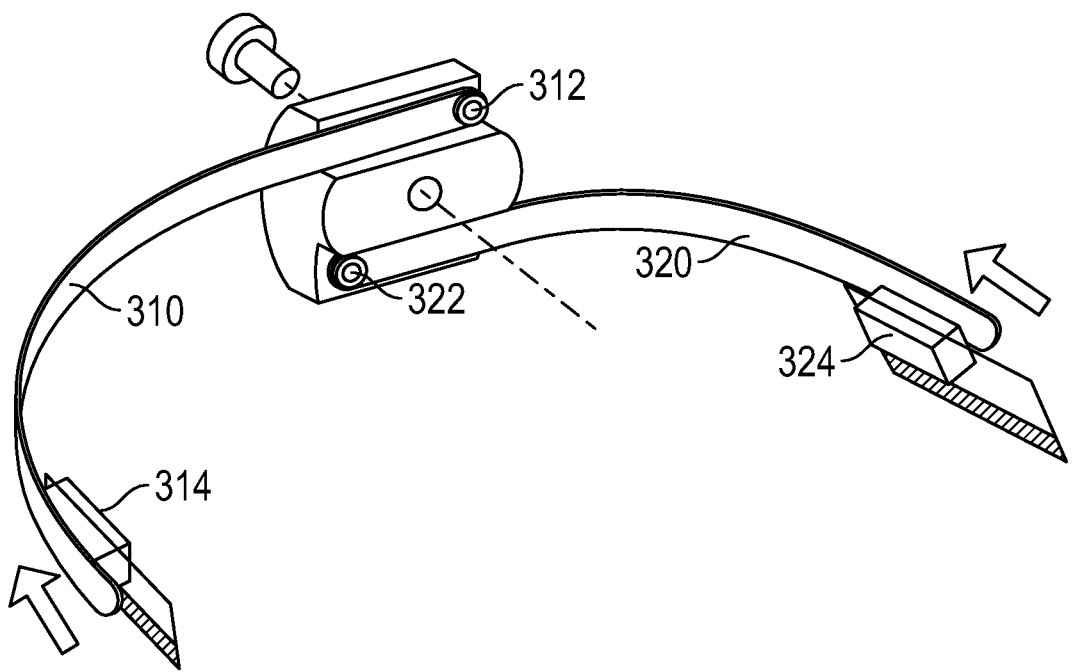
FIG. 7 is a rear sectional view of an embodiment of the adjustment knob in the open position.
Figure 8:
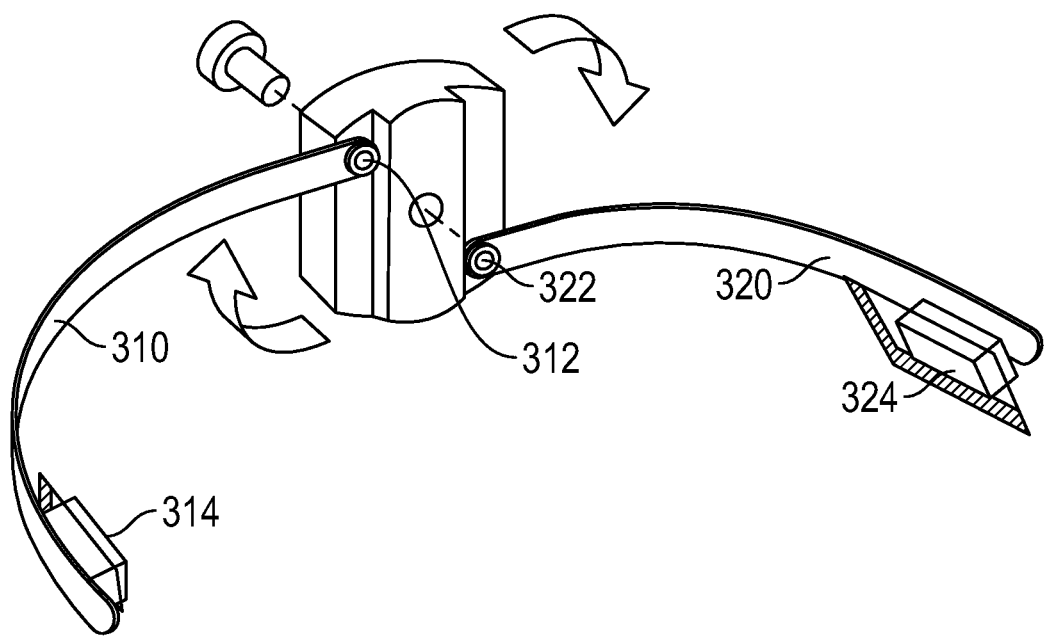
FIG. 8 is a rear sectional view of an embodiment of the adjustment knob in the closed position.

In referencing the locking mechanism in FIGS. 6-8, a first lateral arm 310 has a first post 312 at the first proximal end 311 thereof that cooperates with the adjustment knob 210, which has a first knob opening 301, that engages the first post 312 and a second knob opening 302 that engages a second post 322 on the second lateral arm 320. The first and second openings 301, 302 may be at opposing ends so that turning the knob in one direction will push or pull the lateral arms 310, 320 in the same direction, either toward each other simultaneously or away from each other simultaneously, to lock or release the height adjustment mechanism 200.

The first distal end of 313 the first lateral arm 310 may comprise a first incline projection 314 that may engage a first panel incline slot 331 on the first locking panel 330 and a first body incline slot 337 (not shown) on the lateral body portion 184. The second distal end of 323 (not shown in FIGS. 3-5) the second lateral arm 320 (not shown in FIGS. 3-5) may comprise a second incline projection 324 that engages a second panel incline slot 341 (not shown) on the second locking panel 340 (not shown) and a second body incline slot 347 (not shown) on the lateral body portion 194.

In some aspects, the first and second knob openings 301, 302 (not shown) cooperate with posts 321, 322 and are positioned so that turning the adjustment knob 210 will unlatch the incline projections 314, 324 of the lateral arms 310, 320 from the panel incline slots 331, 341 (341 not shown) simultaneously.

The dotted lines (FIG. 6) show where the position of the incline projection 314, 324 will move once the adjustment knob 210 is opened, for example, by turning it such as by 45°-90°. FIG. 7 shows an embodiment of the adjustment knob 210 in the open position. FIG. 8 shows an embodiment of the adjustment knob 210 in the closed position.

In some aspects, the first locking panel 330 may comprise a first panel spring mechanism 333, such as a compression spring, leaf spring or deforming body, that bias the first locking panel 330 to a locked position whereby the first row of teeth 332 of the first locking panel 330 engage first opposing teeth 335 on the first latch 334. When the incline projection 314 is unlatched, the first row of teeth 332 become disengaged from the first opposing teeth 335 of the first latch 334.

The first latch 334 moves by the spring force such as by the first deforming body 160 when unlatched and engages the first locking panel 330 when latched. The first latch 334 may be coupled to a first latch coupler 336, such as a rivet or flange/screw that may be positioned through and rides along a path defined by both a first chin elongate slot 136 and first body elongate slot 187.

In some aspects, the first locking panel 330 may comprise a first panel spring mechanism 333, such as at least one a compression spring, leaf spring or deforming body, that bias the first locking panel 330 to a locked position whereby the first row of teeth 332 of the first locking panel 330 engage first opposing teeth 335 on the first latch 334. When the first incline projection 314 may be unlatched, the first row of teeth 332 become disengaged from the first opposing teeth 335 of the first latch 334.

Similarly on a second side, the second latch 344 moves by the spring force of the second deforming body 161 when unlatched and engages the second locking panel 340 when in a locked position. The second latch 344 may be coupled to a second latch coupler 346, such as a rivet or flange and screw that may be positioned through and rides along, a path defined by both a second chin elongate slot 146 and second body elongate slot 197.

Thus, a path may be defined along which latches 334, 344 travel that will allow the chin portion 130 to be raised or lowered in relation to the body portion 170.

Further, in some aspects, the second locking panel 340 (not shown) may comprise a second panel spring mechanism 343 (not shown), such as at least one compression spring, leaf spring or deforming body, that bias the second locking panel 340 (not shown) to a locked position whereby the second row of teeth 342 (not shown) of the second locking panel 340 (not shown) engage second opposing teeth 345 (not shown) on the second latch 344 (not shown). When the second incline projection 324 may be unlatched, the second row of teeth 342 become disengaged from the second opposing teeth 345 of the second latch 344.

In some aspects, the panel spring mechanisms 333, 343 may comprise a pair of compression springs 333a, 333b, 343a, 343b positioned at either ends of the locking panels 330, 340. The panel spring mechanisms 333, 343 may be in the resting state when the row of teeth 332, 342 and the opposing teeth 335, 345 are engaged. When the incline projections 314, 324 are unlatched, the springs are compressed.

In some aspects, the locking panels 330, 340 may be coupled to the lateral body portions 184, 194 respectively such as through pairs of first and second rivets 338a, 338b, 348a, 348b (not shown) that are fixed to the lateral body portions 184, 194. The locking panels 330, 340 may have corresponding pairs of first and second panel rivet slots 339a, 339b, 349a, 349b for receiving the rivets 338a, 338b, 348a, 348b so that they are slideably engaged and may move along the panel rivet slots 339a, 339b, 349a, 349b. Further, a pair of compression springs 333a, 333b, 343a, 343b may also be located within or proximate the panel rivet slots 339a, 339b, 349a, 349b.

In some aspects, locking panels 330, 340 have panel incline slots 331, 341 (341 not shown) running along their length that roughly align with body incline slots 337, 347 (not shown) on the lateral body portions 184, 194 respectively underneath the panel incline slots 331, 341. The panel incline slots 331, 341 and the body incline slots 337, 347 have similar lengths for accepting the incline projections 314, 324, and may be longer than the incline projections 314, 324. The panel incline slots 331, 341 however may be wider than the body incline slots 337, 347.

In some aspects, the body elongate slots 187, 197, panel incline slots 331, 341, and body incline slots 337, 347 may be positioned at any appropriate angle that will allow the anterior component to function properly (such as an approximately a 45° angle) relative to the horizontal midplane that roughly extends from the center of the opening between the chin portion 130 and the body portion 170 toward the center of the deforming portions 160, 161. The exact location of the midplane and size of the angles are not defined as critical elements but rather may be useful in discussing the relationship among the moving parts. The movement of the latches 334, 344 in the body elongate slots 187, 197, and the movement of the incline projections 314, 324 in the panel incline slots 331, 341 and body incline slots 337, 347 may be referred to as moving in a parallel direction. In some aspects when unlatched, however, the rows of teeth 332, 242 of the locking panels 330, 340 may move away from the opposing teeth 335, 345 and thus move perpendicularly to this parallel direction.

Specifically, panel incline slots 331, 341 may be longer and wider than the incline projections 314, 324 and allows for locking panels 330, 340 to move perpendicularly (side to side across the width of panel incline slots 331, 341) relative to the parallel direction. The disengagement of the incline projections 314, 324 from the panel incline slots 331, 341 may force the locking panels 330, 340 in a direction perpendicular to the parallel direction, which disengage the rows of teeth 332, 342 from the opposing teeth 335, 345 of the latches 334, 344.

The lateral arms 310, 320 may cooperate with one or more guides 350, 351 (351 not shown) to help keep lateral arms 310, 320 (320 not shown) in place. In addition, a housing (not shown) for the lateral arms 310, 320 may serve as a guide thereby allowing the incline projections 314, 324 to ride in the panel incline slots 331, 341 (341 not shown). A housing (not shown in FIGS. 6-8) may also comprise an opening (not shown) to hold the adjustment knob 210 in place and additional fittings or knobs (not shown) to operate the adjustment knob 210 from outside the housing.

Figure 30A:
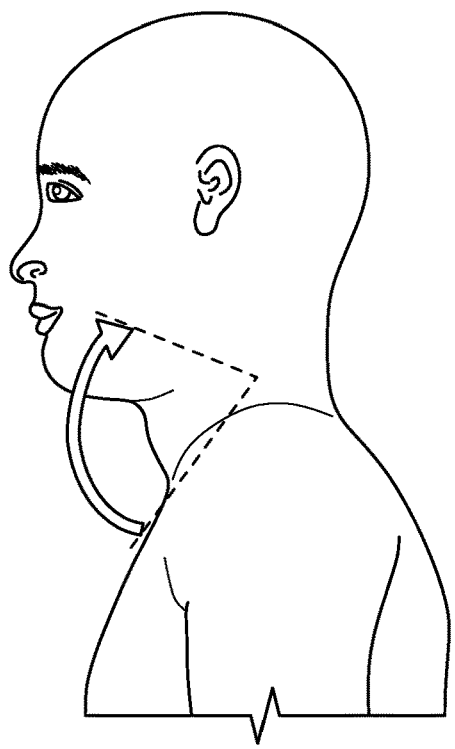
FIG. 30a demonstrates the angle between a conventional chin portion and body portion having a pivot point therebetween, for example, using a height adjustment mechanism comprising a typical camming rotation, which may retract the chin portion into the coronal plane of the body when in use.
Figure 30B:
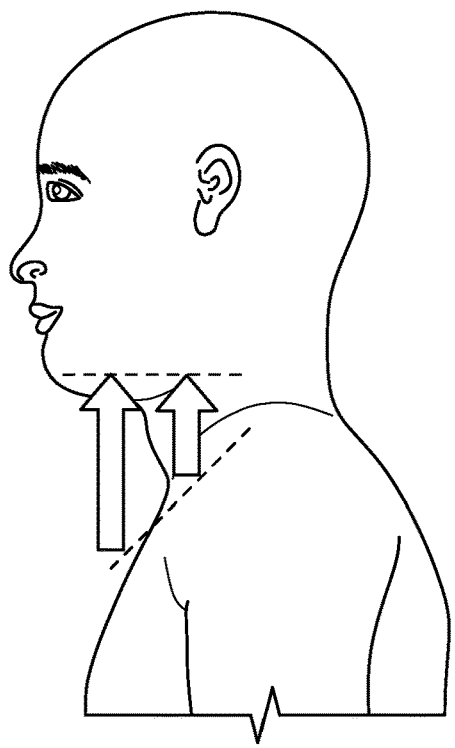
FIG. 30b demonstrates aspects of the height adjustment mechanisms herein illustrating the substantially vertical height adjustment, wherein the chin portion is lifted substantially parallel to the coronal plane and perpendicular to the transverse plane of the body when in use.

Another embodiment of the height adjustment mechanism provides a four bar adjustment mechanism. In some aspects, the adjustment of the four bar adjustment mechanism provides substantially parallel motion and substantially vertical lift, which better conforms to the anatomy of a neck in comparison to conventional cervical collars that incorporate pivot mechanisms to raise the chin piece. (See FIG. 30.) For example, patients having larger trapezius muscles, a shorter distance from the shoulder to ear, and/or larger necks, for example in the case of obese patients, benefit from at least substantially vertical adjustment providing more robust mandible support while preventing the chin from moving up at an angle while the neck bends back.

Referring to FIGS. 9-16, embodiments of an anterior component 100 of a cervical collar may comprise a chin portion 130 and a body portion 170 and a four bar adjustment mechanism 200. The chin portion 130 may further comprise a first lateral chin piece 135 having a first chin elongate slot 136 for receiving a first chin sliding rivet 418; a second lateral chin portion 145, having a second chin elongate slot 146 for receiving first chin sliding rivet 428; and a chin rest 150, for resting the chin of a user.

The chin portion 130 and body portion 170 may be coupled to a pair of cross bars 410a, 410b, 420a, and 420b. The first cross bars 410a, 410b, are moveably connected at the center portions thereof with a first central coupler 417, and second cross bars 420a, 420b, are moveably connected at the center portions thereof with a second central coupler 427.

In some aspects, referring to FIGS. 11-15, the four bar adjustment mechanism 200 may further comprise actuator bars 430, 440 that are each connected to one of the cross bars 410a, 420a, on one end of each and on the other end to a first shuttle 455 and a second shuttle 465 that cooperate with a first lead screw 454 and a second lead screw 464. The shuttles 455, 465 may engage at least a portion of the male threads 458, 468, and may partially (FIG. 11), or fully surround (FIGS. 13-14) the lead screws 454, 464 respectively. The shuttle length may be shorter or longer and/or may engage or surround more or less threads than depicted. The terms lead screw nut and lead screw shuttle are used interchangeably.

In some aspects, the first lead screw 454 rests in a first carrier 456 that allows the first lead screw 454 to rotate in place. Similarly, the second lead screw 464 rests in a second carrier 466 that allows the second lead screw 464 to rotate in place. Each of the carriers 456, 466, may contain one, two or more curved portion for receiving an end of each of the lead screws 454, 464. The carriers 456, 466, may be a separate piece or integral with the body portion 170.

In some aspects, one end of the first lead screw 454 may terminate in a first bevel gear 459 and one end of the second lead screw 464 may terminate in a second bevel gear 469, which engage a drive gear 470. An end of each of the lead screws 454, 464 may contain a first bevel gear 459 and a second bevel gear 469 that each engages a drive gear 470. Relevant aspects of the lead screw assembly discussed herein, apply here as well, for example, relating to the benefits of using a lead screw. Rotating the drive gear 470, for example using a drive knob 476, rotates each of the first bevel gear 459 and the second bevel gear 469 attached to each of the lead screws 454, 464. The lead screws 454, 464 each engages shuttles 455, 465 that travel along the shuttle slots 457, 467 (obscured behind lead screws, e.g., FIG. 12), and move the actuator bars 430, 440. (In some aspects, referring to FIGS. 9-10, the anterior component may contain a sliding actuator 210, and actuator bars 430, 440. Aspects of these portions of the anterior component 100 are recited below in more detail.)

The first actuator bar 430 may be moveably connected to cross bar 410a at a first body sliding end 414 thereof by a first body sliding rivet 416 that rides in first body elongate slot 187. The second actuator bar 440 may be moveably connected to a cross bar 420a at a second body sliding end 424 thereof by a second body sliding rivet 426 that rides in the second body elongate slot 197.

Referring to FIGS. 9-16, on a first side, the cross bar 410a may be attached at a first chin pivot end 412 thereof by a first chin pivot rivet 413. In some aspects, the first chin pivot rivet 413 may rotatably move but may be otherwise in a stationary position near a first distal end of a first lateral chin portion 135. The cross bar 410b may be moveably connected at a first chin sliding end 411 thereof by a first chin sliding rivet 418 that rides in the first chin elongate slot 136. The cross bar 410b may be moveably connected at a first body pivot end 415 thereof by a first body pivot rivet 419. In some aspects, the first body pivot rivet 419 may rotatably move but may be otherwise in a stationary position and may be paired to an opening near a first distal end of the first lateral body portion 184.

Similarly, on the other second side, the cross bar 420a may be attached at a second chin pivot end 422 thereof by a second chin pivot rivet 423. In some aspects, the second chin pivot rivet 423 may rotatably move but may be otherwise in a stationary position near the second distal end of the second lateral chin portion 145. The cross bar 420b may be moveably connected at a second chin sliding end 421 thereof by a second chin sliding rivet 428 that rides in the second chin elongate slot 146. The cross bar 420b may be moveably connected at a second body pivot end 425 thereof by a second body pivot rivet 429. In some aspects, the second body pivot rivet 429 may rotatably move but may be otherwise in a stationary position and may be paired to an opening near a first distal end of the second lateral body portion 194.

In some aspects, to operate the collar, the drive knob 476 is rotated, which rotates the drive gear 470, which in turn rotates each of the lead screws 454, 464 attached to the shuttles 455, 465 and actuator bars 410, 440, which in turn engage the cross bars 410a, 410b, 420a, and 420b to lift or lower the chin portion.

Figure 9:
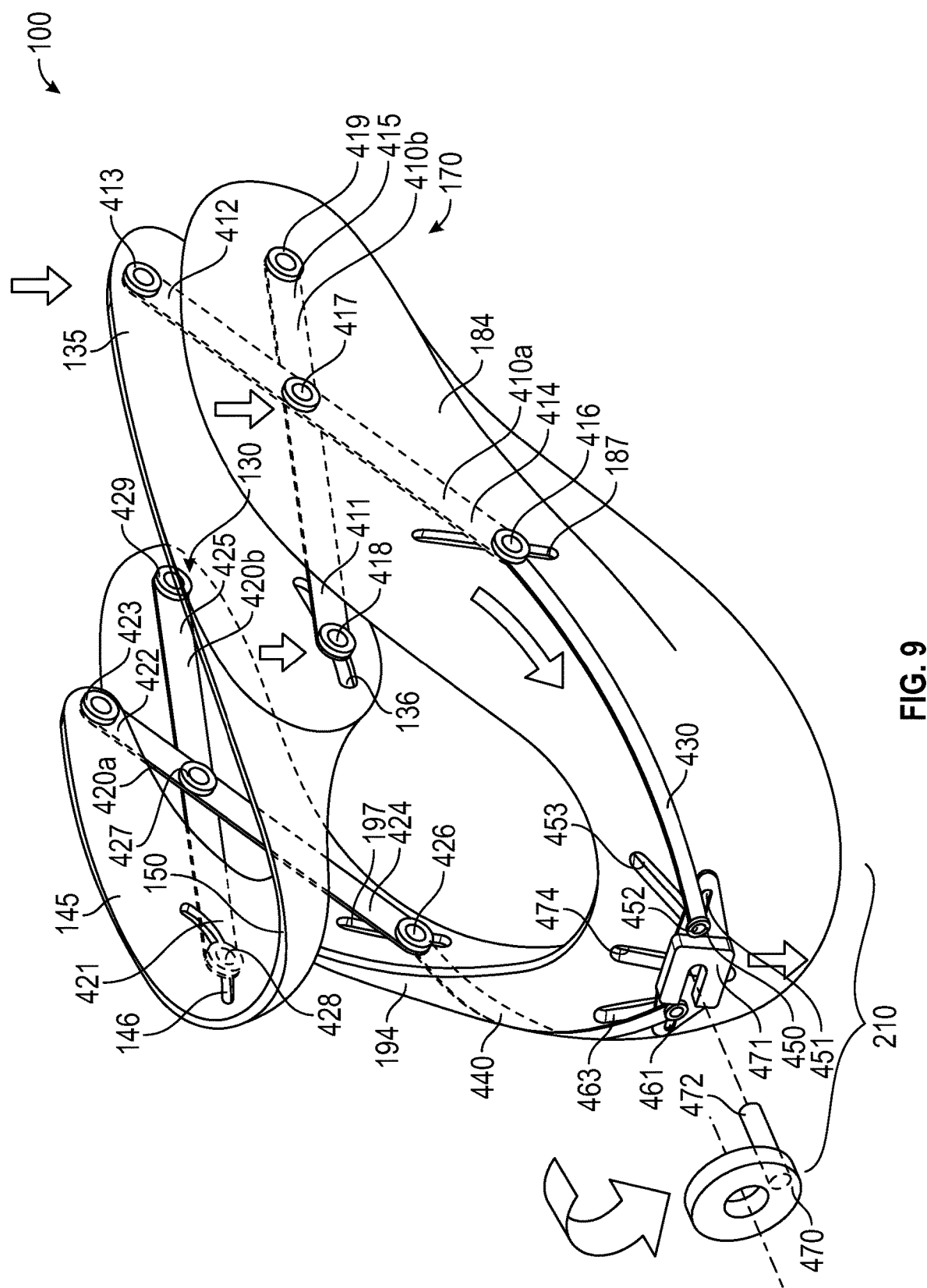
FIG. 9 is a front perspective view of an embodiment of an adjustable anterior component of a cervical collar cervical collar in a closed position before an adjustment is made using a sliding actuator.
Figure 10:
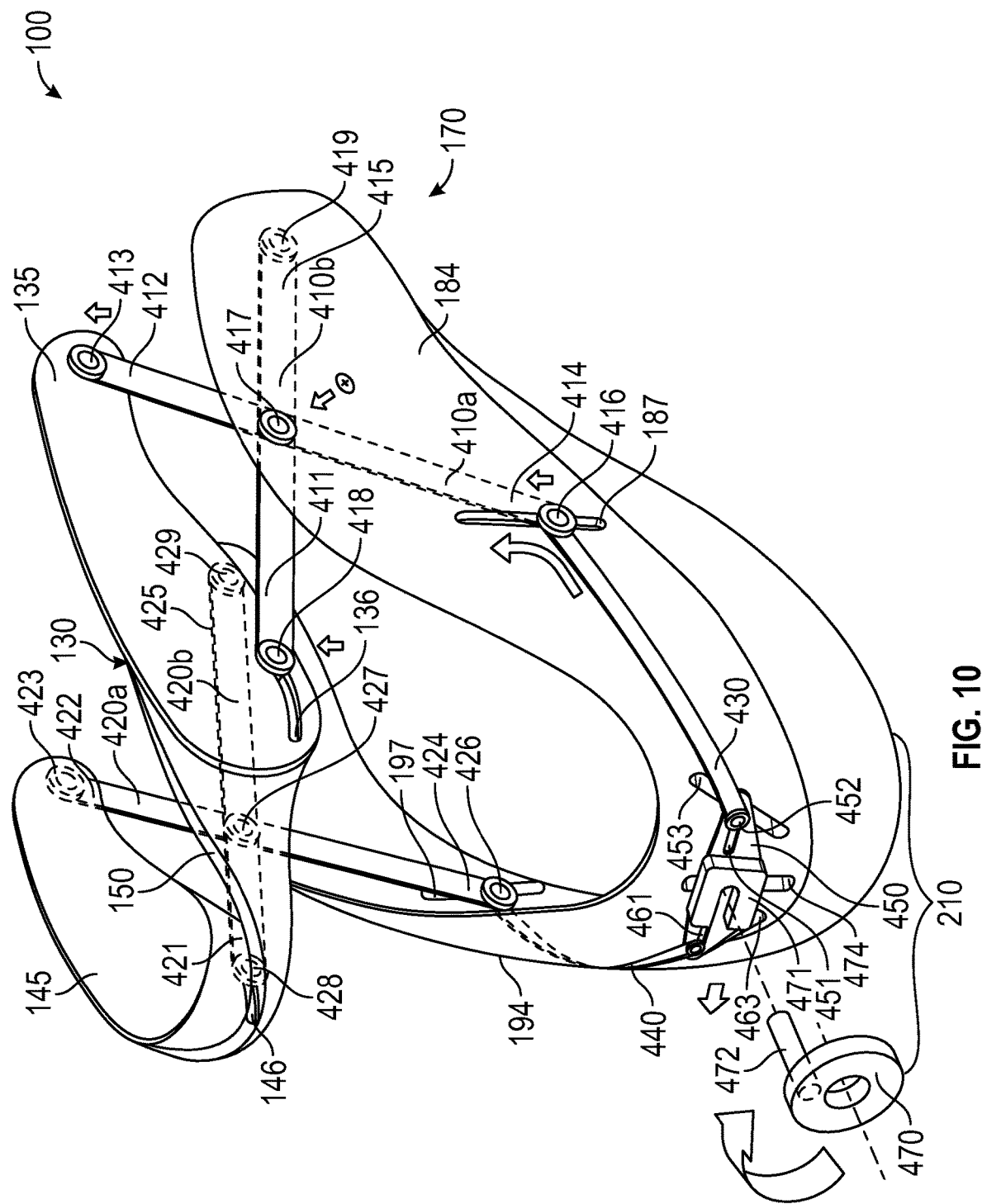
FIG. 10 is a front perspective view of an embodiment of an adjustable anterior component of a cervical collar in an open position after an adjustment is made using a sliding actuator.
Figure 11:
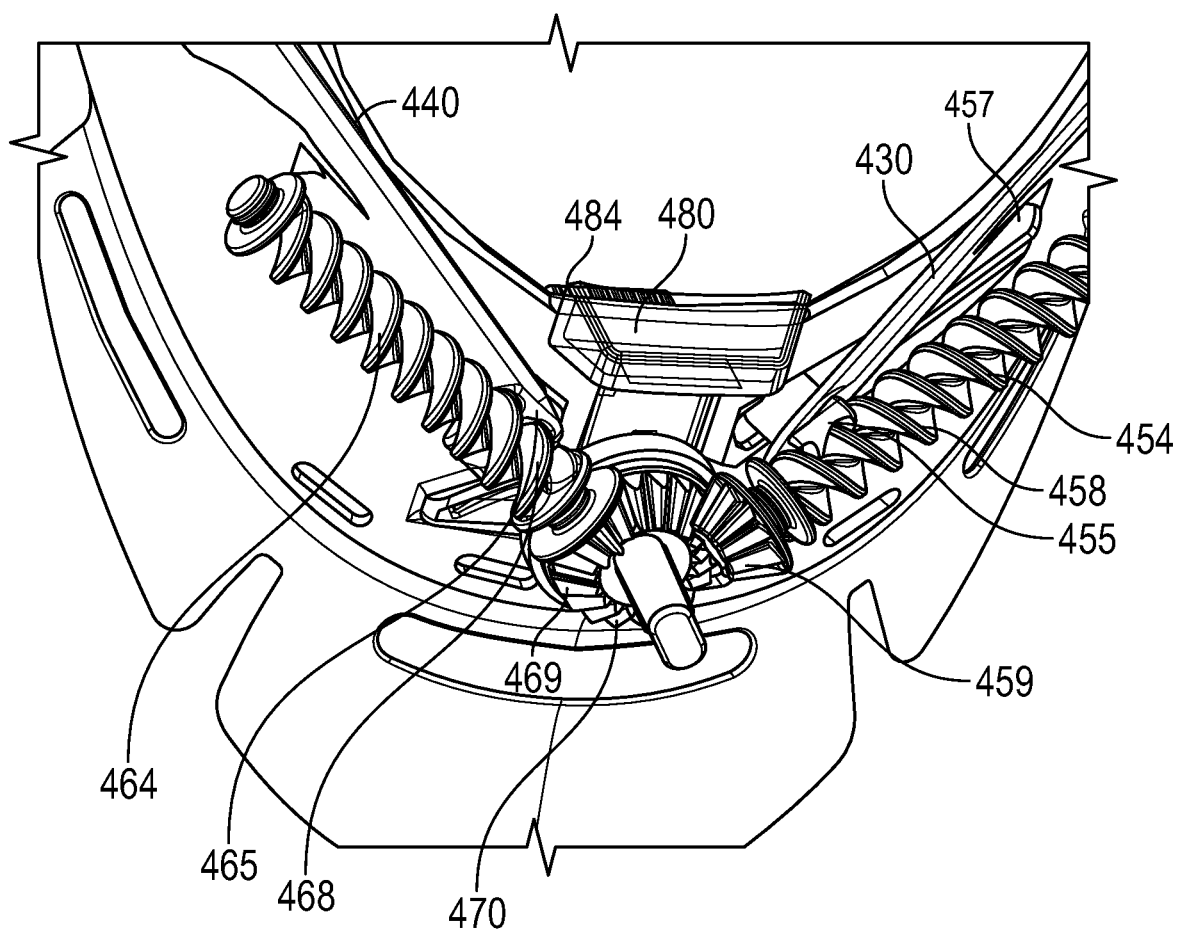
FIG. 11 is an enlarged cut-away view of an embodiment of an adjustable anterior component of a cervical collar using a lead screw nut that does not surround the lead screw.
Figure 12:
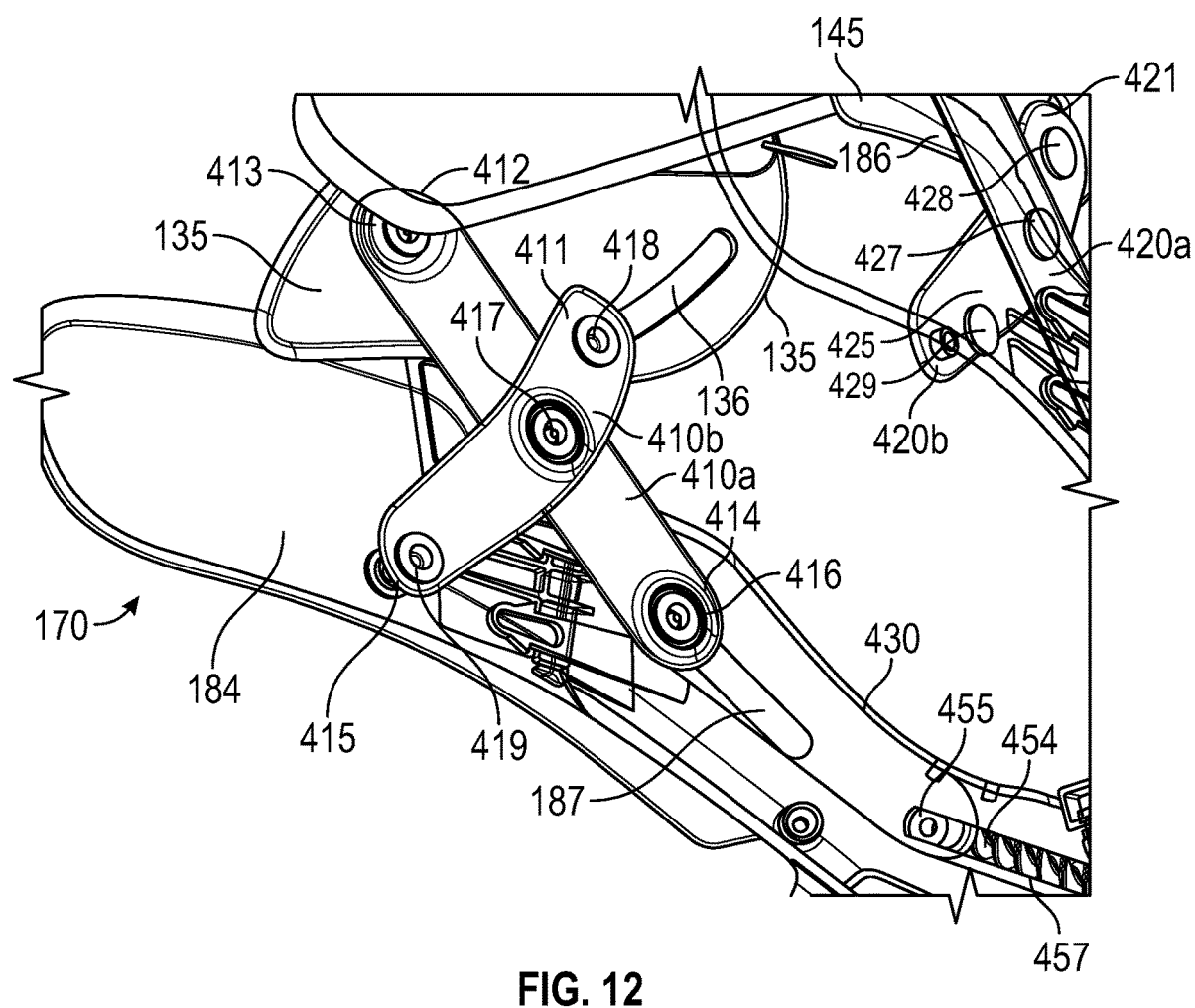
FIG. 12 is a bottom perspective view of features of an embodiment of a height adjustable cervical collar.
Figure 13:
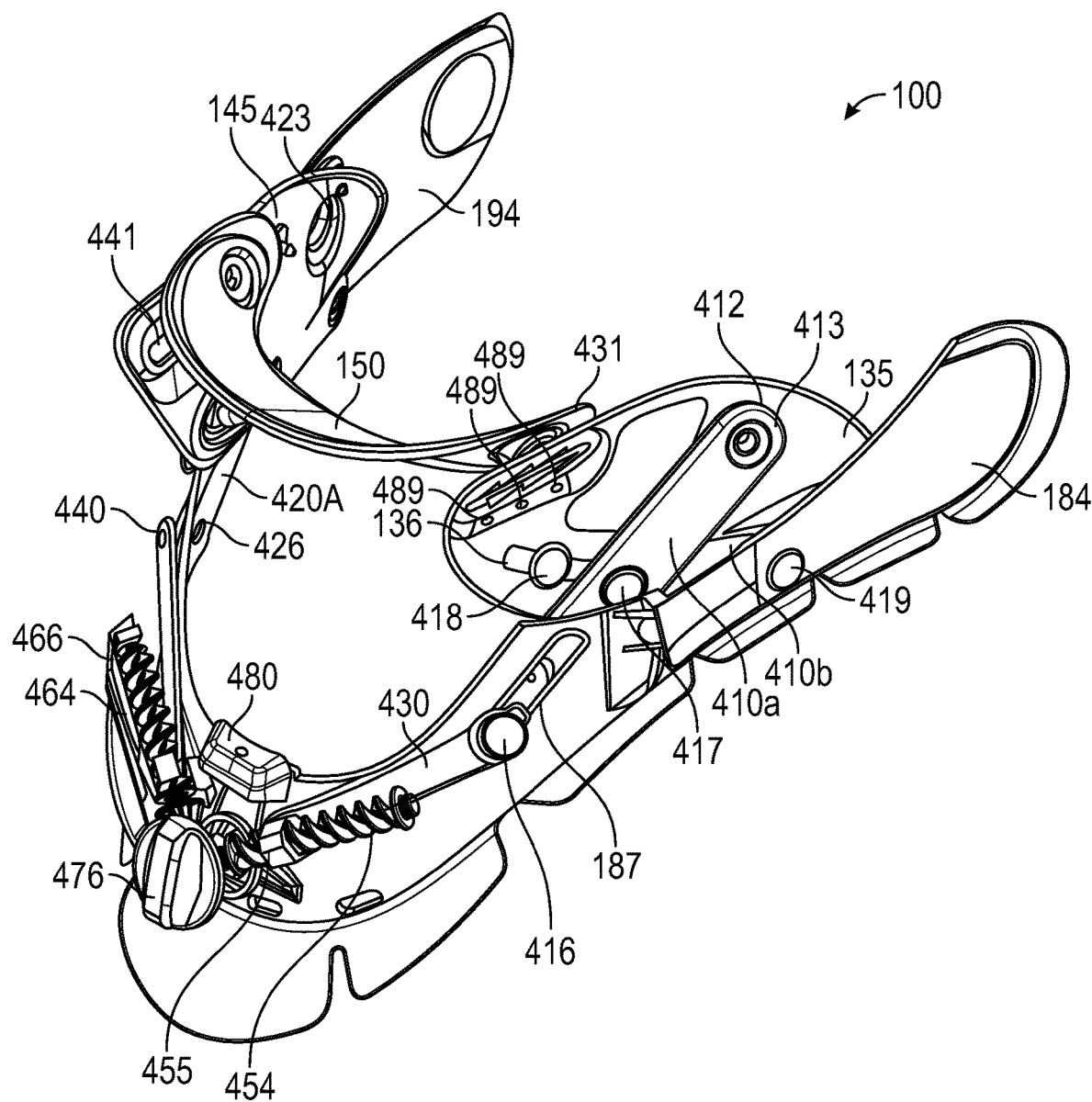
FIG. 13 is a three quarter perspective view of an embodiment of an adjustable anterior component of a cervical collar in a closed position before an adjustment is made using a knob, bevel gears and lead screw nuts that surround the lead screw.
Figure 14:
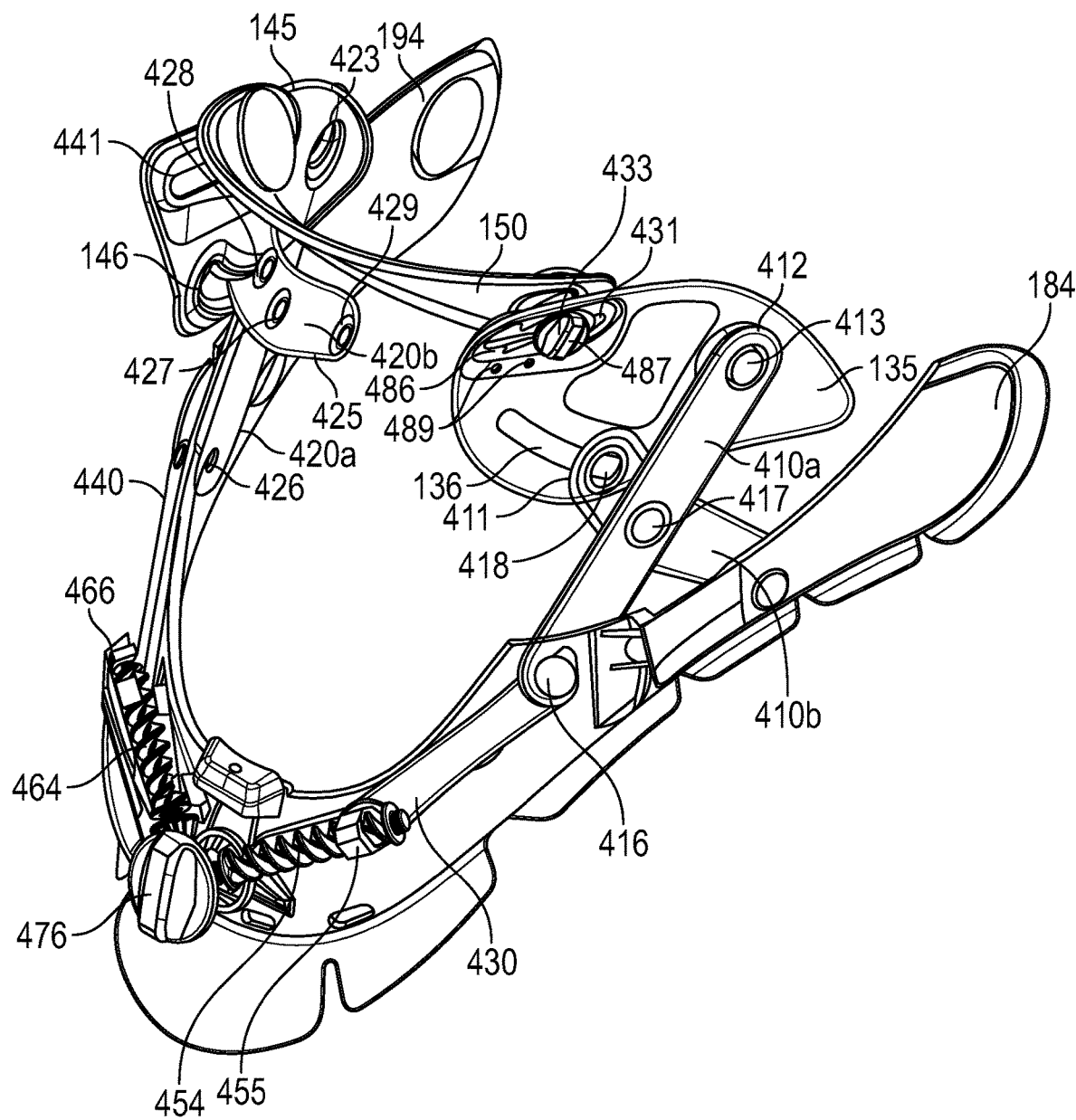
FIG. 14 is a three quarter perspective view of an embodiment of an adjustable anterior component of a cervical collar in an open position after an adjustment is made using a knob, bevel gears and lead screw nuts that surround the lead screw.
Figure 15:
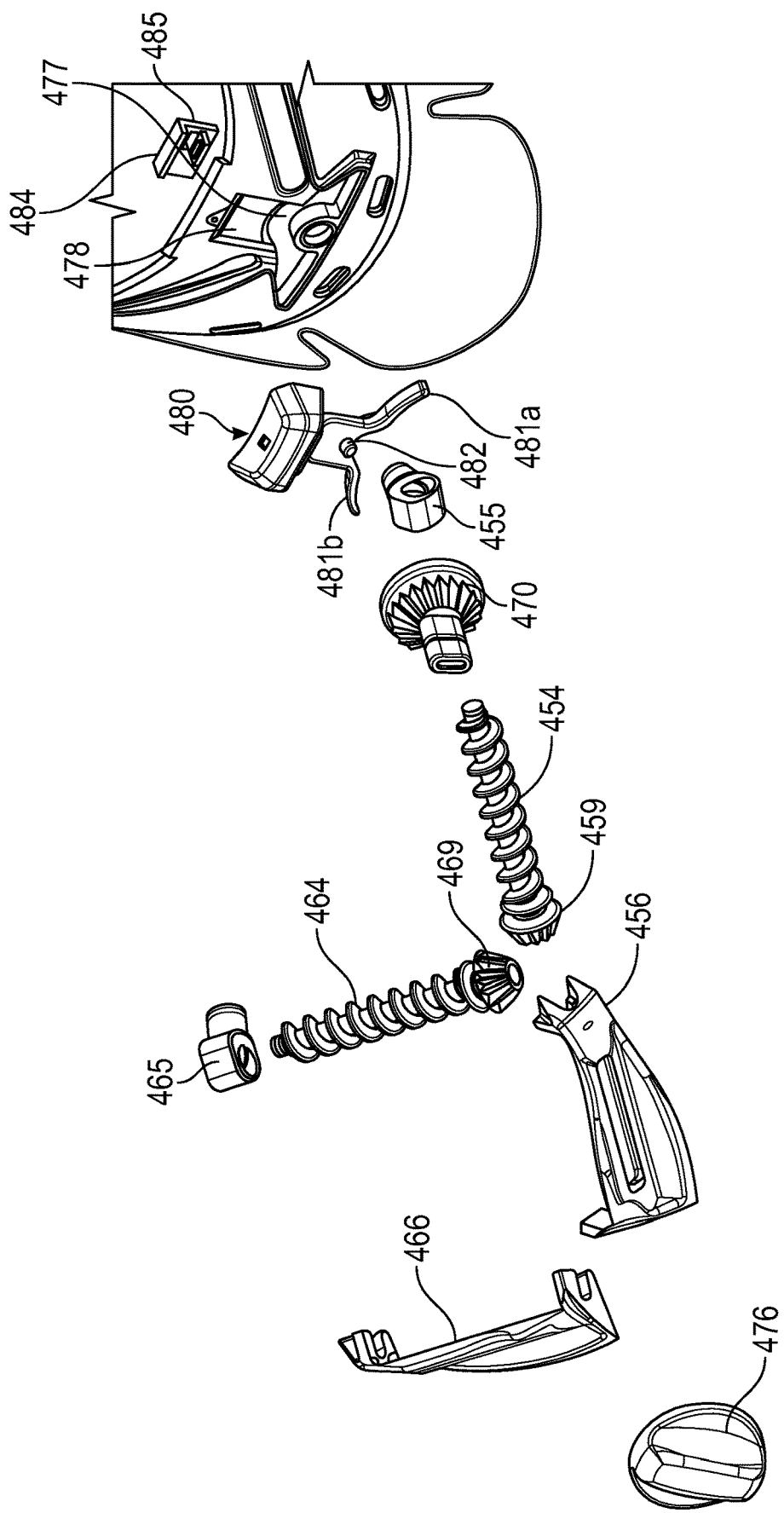
FIG. 15 is an exploded view of an embodiment of a bevel gear mechanism and locking mechanism.
Figure 16:
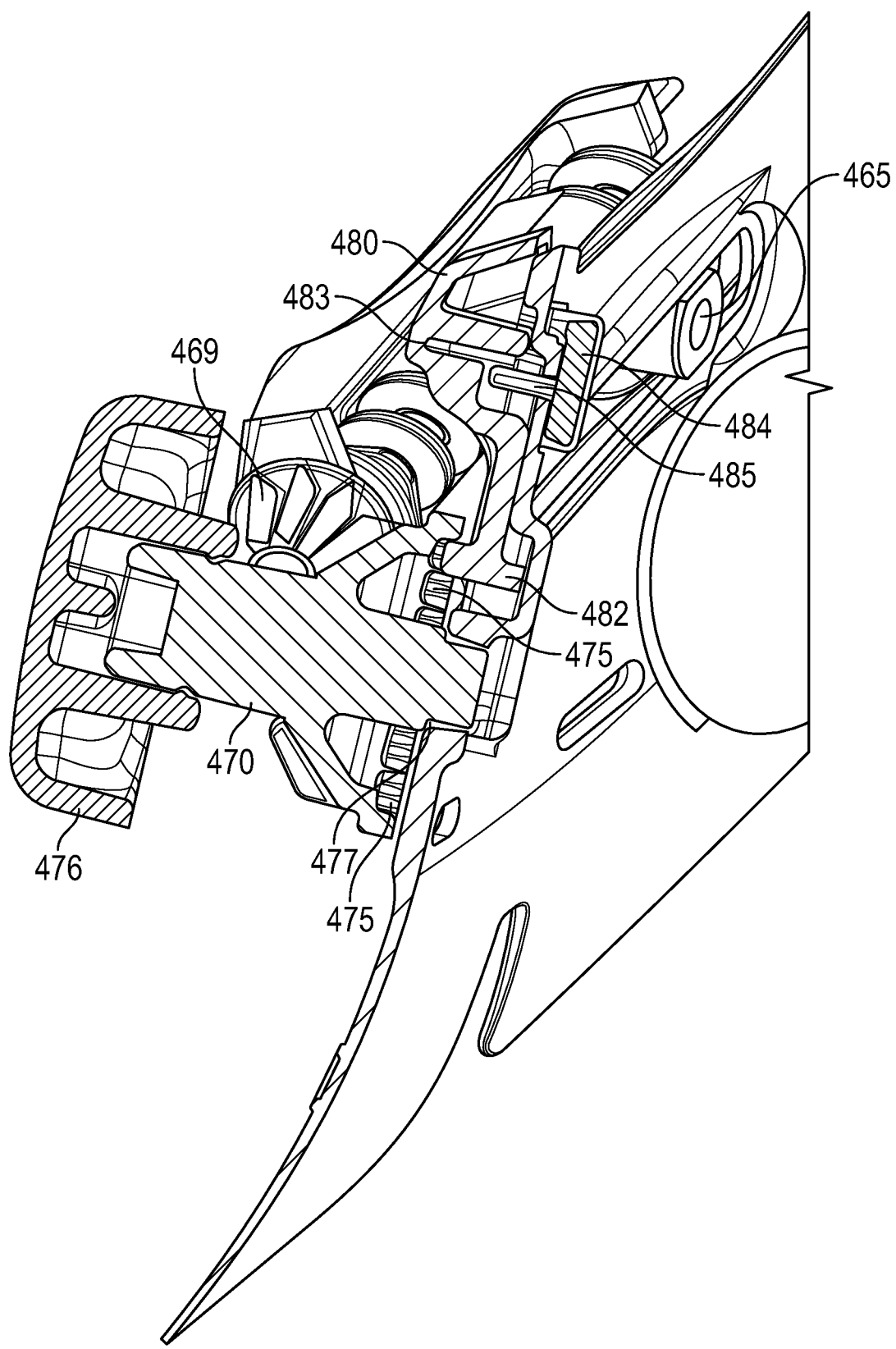
FIG. 16 is a cut away view of an embodiment of a drive gear and locking mechanism.

Referring to FIGS. 9-10, in some aspects, sliding actuator 210 may comprise a sliding plate 450 and an internal knob 470. The sliding plate 450 may comprise lateral slots, a first plate slot 451, second plate slot 461, on either side for accepting first plate sliding rivet 452 and second plate sliding rivet 462 which are attached to proximal ends of first and second actuator bars 430, 440 and rides in first actuator elongate slot 453 and second actuator elongate slot 463 respectively on the body portion 170. The sliding plate 450 further may comprise a central bar 473 (not shown) that rides in a vertical slot 474 in the central portion 175 of the body portion 170. Opposite the central bar 473 on the sliding plate 450 may be a cam groove 471 for accepting a cam follower 472 for adjusting the height of the chin portion 130.

The cam follower 472 can engage the sliding plate 450 and move in a vertical direction, which can be manipulated by an external fitting or knob 476.

In some aspects, when in use, the collar may be positioned by a medical professional, who operates the sliding actuator 210 (or drive knob 476) which causes first and second actuator bars 430, 440 to simultaneously move cross bars 410a and 420a, which are connected by body sliding rivets 416 and 426 that ride in the first and second body elongate slots 187, 197 on the body portion, and which are centrally connected to and therefore cooperate with cross bars 410b and 420b respectively. In turn, cross bars 410b and 420b have chin sliding rivets 418 and 428 attached to one of their ends that ride in their respective first and second chin elongate slots 136, 137 on the chin portion 130. The slots allow simultaneous vertical travel between the chin portion 130 and the body portion 170 when the sliding actuator 210 (or drive knob 476) may be operated, that is, slid (or turned) in one direction or slid (or turned) in the opposite direction to raise or lower the chin portion 130 with respect to the body portion 170 to conform to the neck length and anatomy of an individual patient, when adjusted using a height adjustment mechanism 200.

The chin portion 130 and a body portion 170 herein may comprise substantially rigid material that may provide a supportive framework of the chin portion 130 and the body portion 170. The cross bars and actuator bars may be made from a material that has sufficient stiffness and strength so it can withstand the push and pull of the sliding actuator.

Referring to FIGS. 13-16, in some aspects the collar may comprise a locking mechanism. The locking mechanism may comprise a lock button 480 that may be useful for releasing the gear drive to set a collar height. In some aspects, the lock button 480 may comprise leaf springs 481a and 481b and a lock button tooth 482. The lock button tooth 482 on the lock button 480 engages internal gear teeth 475 that may be found in the internal diameter of the drive gear 470. In some aspects, leaf springs 481a and 481b on the lock button 480 maintain the lock button tooth 482 in an engaged position with the drive gear internal diameter gear teeth 475 as shown in the cross section of FIG. 16. Pushing downward on the lock button 480 disengages the lock button tooth 482 and allows the drive gear 470 to be rotated, which, in turn, raises or lowers the height of the space between the chin portion 130 and the body portion 170.

Further, in some aspects, the locking mechanism may further comprise a lock switch 484 that may be useful for a practitioner to lock the height in a preferred position to prevent a user from easily adjusting the height after a practitioner's fitting. A lock switch 484 may comprise a switch flange 485 that is slidingly coupled to a lock button flange 483 through the switch opening 478 on the housing 111. After a fitting, a practitioner may move the lock switch 484, such as toward the center, so that switch flange 485 engages the lock button flange 483 of the lock button 480. Engaging the lock button flange 483 prevents the lock button 480 from moving, thereby locking the height of the space between the chin portion 130 and the body portion 170. In some embodiments, the switch flange 485 of the lock switch 484 is disengaged from the lock button flange 483 to allow a practitioner or user to adjust the height of the space between the chin portion 130 and the body portion 170.

In some aspects, the anterior component may comprise a chin portion 130 that may comprise a first lateral chin portion 135; a second lateral chin portion 145, and a chin rest 150, therebetween for resting the chin of a user. The chin rest 150 may be integral with the rest of the chin portion 130, or may include a separate component or components.

Regarding an anterior component, for example, comprising a four bar adjustment mechanism, a chin portion 130 may comprise a first lateral chin piece 135 having a first chin elongate slot 136 for receiving a first chin sliding rivet 418; a second lateral chin portion 145, having a second chin elongate slot 146 for receiving second chin sliding rivet 428; and a chin rest 150, for resting the chin of a user. In some aspects, the chin portion 130 may comprise a chin depth adjustment mechanism.

Figures 17A, 17B:
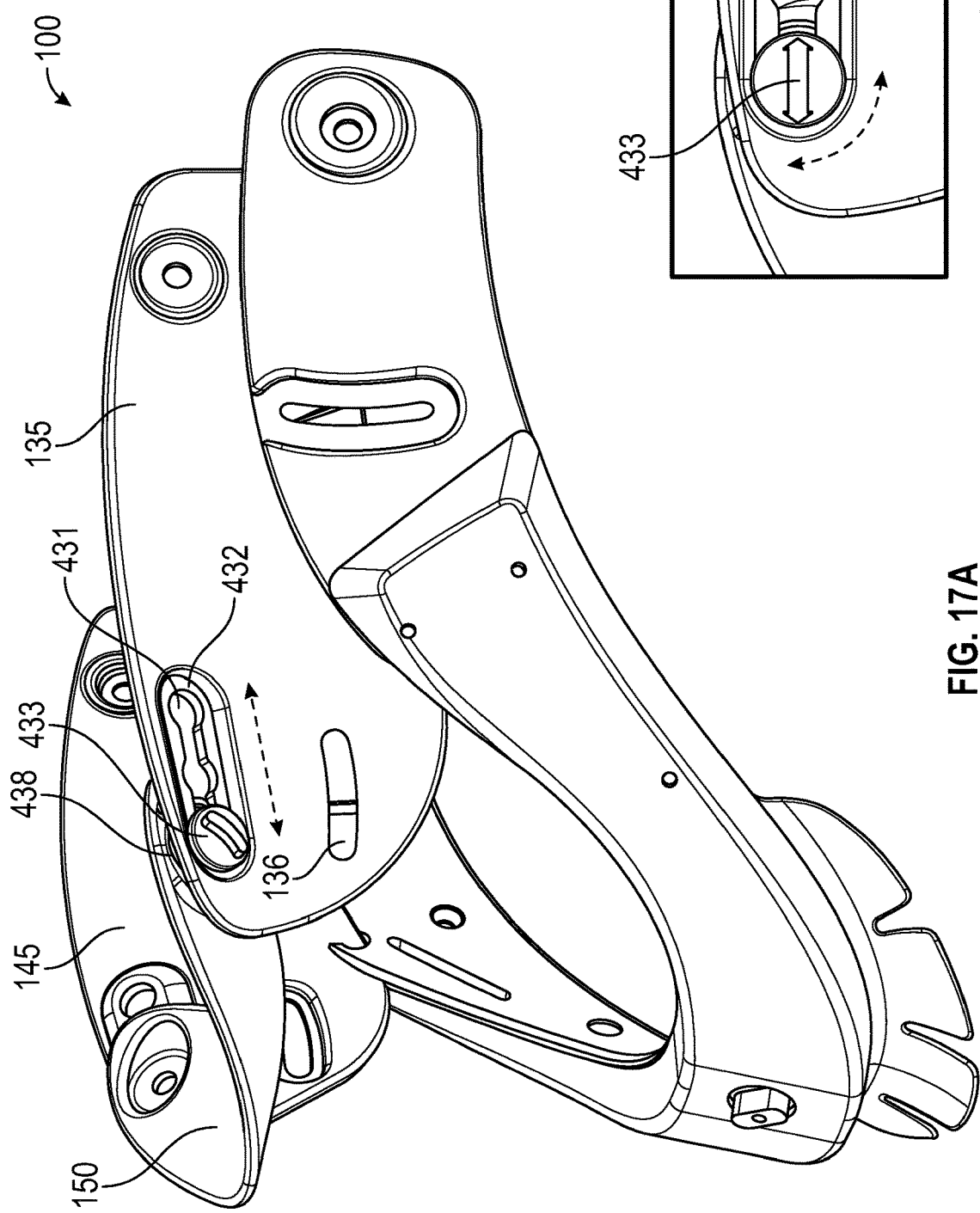
FIG. 17a shows a three quarter perspective view of an embodiment of an adjustable anterior component of a cervical collar having a chin adjustment feature.
FIG. 17b shows an enlarged side view of an embodiment of the adjustable chin locking mechanism.
Figure 18B:
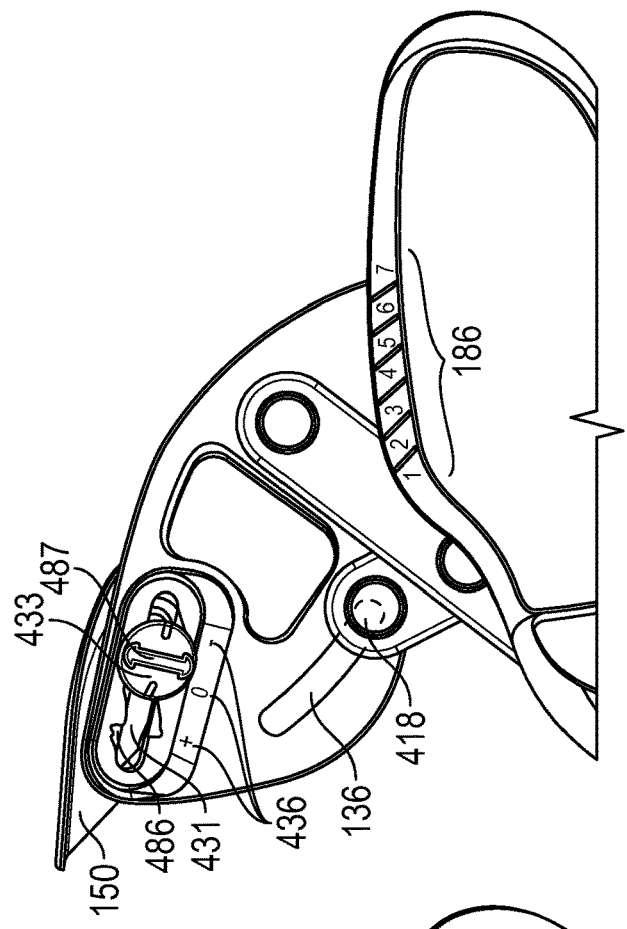
FIGS. 18a and 18b collectively are side views showing an embodiment illustrating pivoting of a chin rest.
Figure 18A:
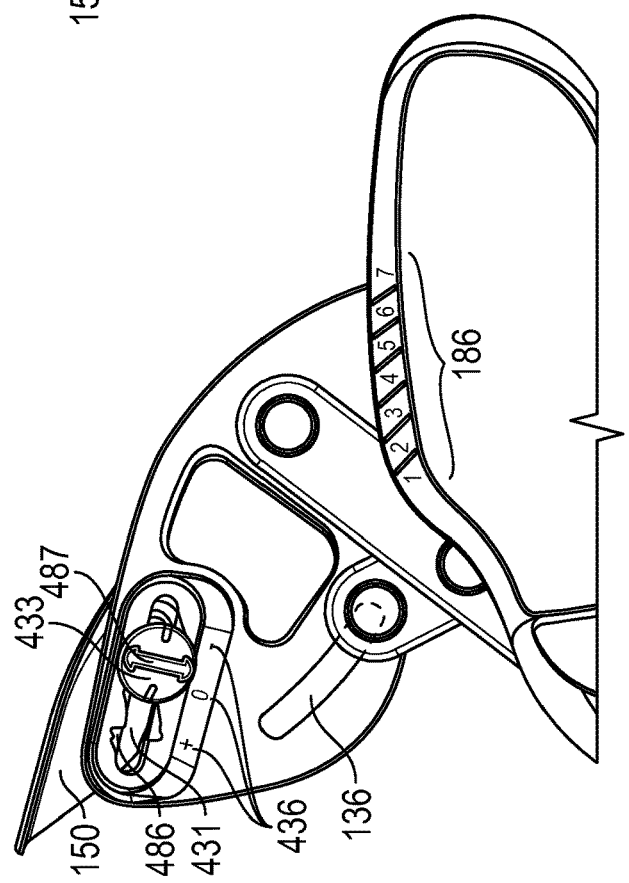
Figure 19:
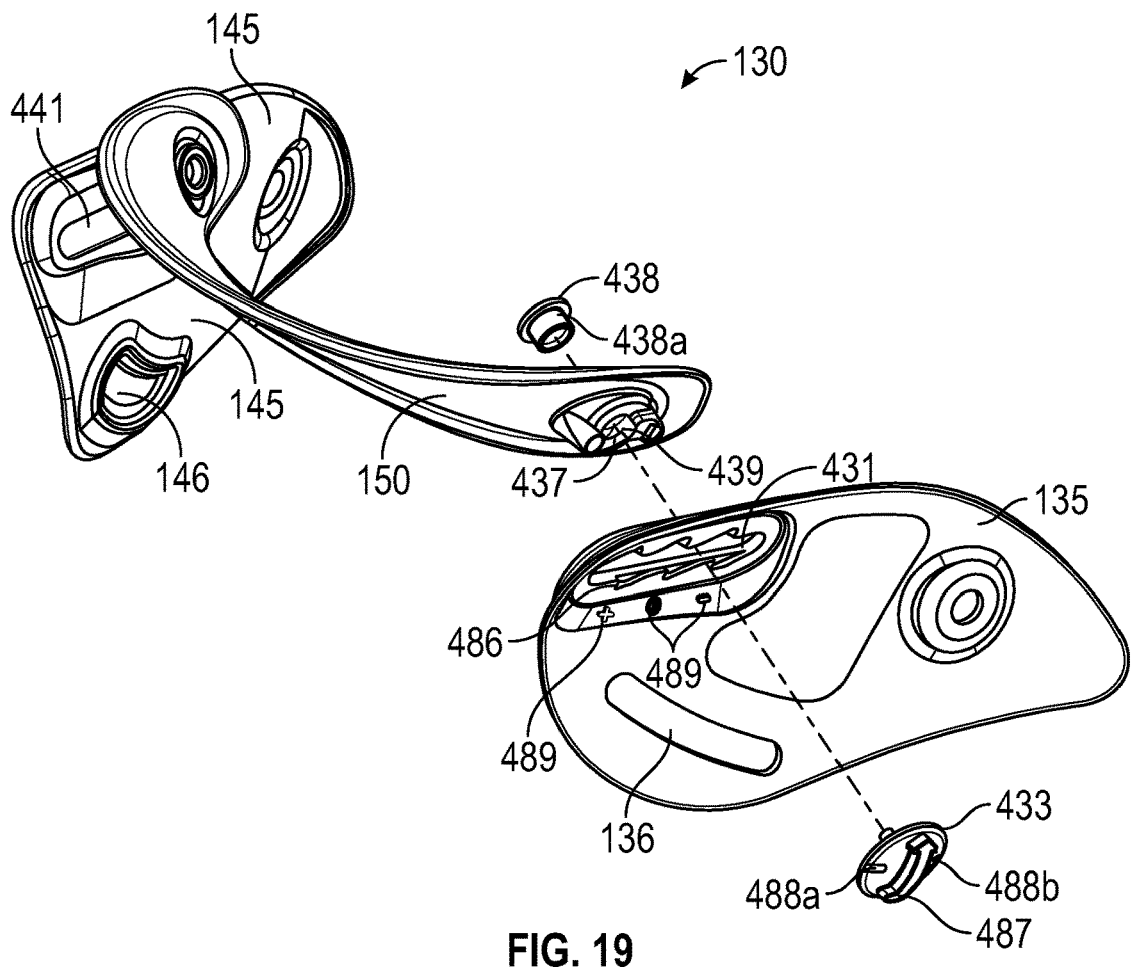
FIG. 19 is an exploded view of an embodiment of a chin adjustment feature.
Figure 20:
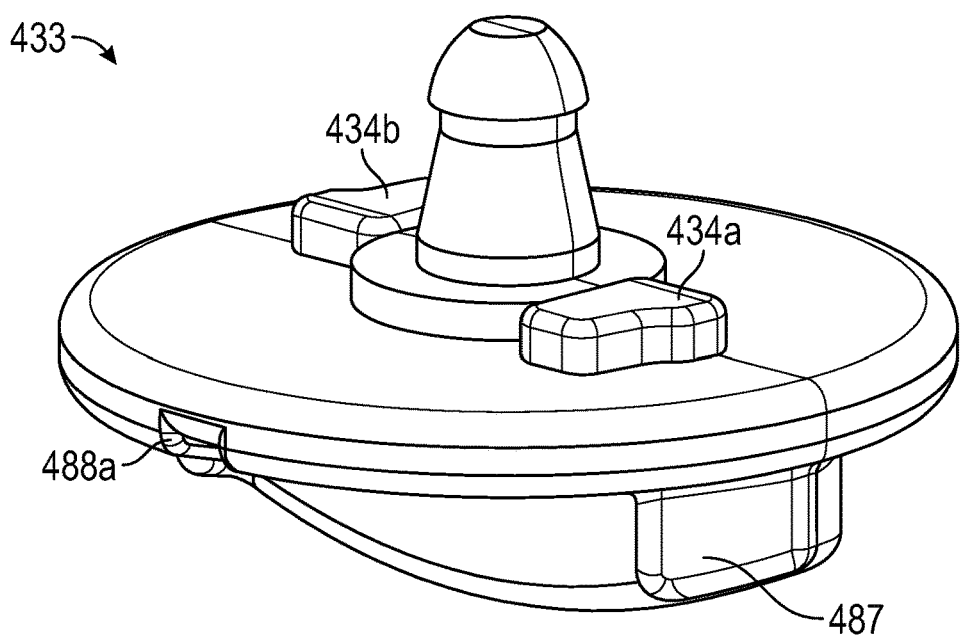
FIG. 20 is a view of an internal side of an embodiment of a male chin rivet of a chin adjustment feature.

Referring to FIGS. 17-19, in some aspects, a chin portion 130 may comprise a separate chin rest 150, which may be adjusted to change the depth of the chin rest (illustrated by approximately horizontal dashed lines in FIG. 17a) to accommodate various users' anatomies. In some aspects, the separate chin rest 150 may have a first chin rest opening 437 that may align with a first depth adjustment slot 431 in the first lateral chin portion 135 to receive a first male chin rivet 433, which mates to a first female chin rivet 438. A first rotation stop 439, which may be separate or integral to the chin rest 150, may be positioned proximate the first chin rest opening 437. The first female chin rivet 438, and the first rotation stop 439, ride in the first depth adjustment slot 431, while the first male chin rivet 433 is in the mated position. The first rotation stop 439 may prevent the female chin rivet 438 from fully rotating, and may have an outer diameter that may be smaller than the height of the first depth adjustment slot 431 allowing the chin rest 150 to pivot slightly, about 10-20 degrees, without fully rotating, to accommodate various users' chin anatomies as illustrated in FIGS. 18a and 18b. The first female chin rivet 438 may be sized so that it fits somewhat snugly in the first depth adjustment slot 431 such that most of weight is carried on the cylindrical portion of the first female chin rivet 438b when in use.

In some aspects, after the separate chin rest 150 is adjusted to fit a user, it may be locked in place. For example, the first male chin rivet 433, which may be mated to the first female chin rivet 438, may be positioned within in the first chin rest opening 437 and rotated to lock the adjusted setting in place. The first male chin rivet 433 may comprise a first male chin rivet indicator 487, such as an arrow that allows the user to orient the first male chin rivet 433 in a locked (such as an arrow that points up and down) or in an unlocked position (such as an arrow that points side to side) or vice versa. In some aspects, the first depth adjustment slot 431 has thinned regions 486 proximate a first engagement surface 432 that engage a first set of locking faces 434a, 434b on the first male chin rivet 433. The first male chin rivet 433 may further comprise first male chin rivet notches 488a, 488b that may be aligned with one of the first chin depth sizing indicia 436, when unlocked, if desired. Once the desired depth adjustment is made, the first male chin rivet indicator 487 may be moved to the locked position (such as an arrow that points up and down). Collectively, these components may be referred to as the first chin rest locking mechanism.

Similarly, the separate chin rest 150 may have a second chin rest opening 447 that may align with a second depth adjustment slot 441 in the second lateral chin portion 145, to receive a second male chin rivet 443, which mates to a second female chin rivet 448. A second rotation stop 449, which may be separate or integral to the chin rest 150, may be positioned proximate the second chin rest opening 447. The second female chin rivet 448 and the second rotation stop 449 ride in the second depth adjustment slot 441, while the second male chin rivet 443 is in the mated position. The second rotation stop 449 may prevent the female chin rivet 448 from fully rotating, and may have an outer diameter that may be smaller than the height of the second depth adjustment slot 441 allowing the chin rest 150 to pivot slightly, about 10-20 degrees, without fully rotating, to accommodate various users' chin anatomies as illustrated in FIGS. 18a and 18b. The second female chin rivet 448 may be sized so that it fits somewhat snugly in the second depth adjustment slot 441 such that most of weight is carried on the cylindrical portion of the second female chin rivet 448b when in use.

Similarly as discussed above regarding the first side, in some aspects, after the separate chin rest 150 is adjusted to fit a user, it may be locked in place. For example, the second male chin rivet 443, which may be mated to the second female chin rivet 448, may be positioned within in the second chin rest opening 447 and rotated to lock the adjusted setting in place. The second male chin rivet 443 may comprise a second male chin rivet indicator 497, such as an arrow that allows the user to orient the second male chin rivet 443 in a locked (such as an arrow that points up and down) or in an unlocked position (such as an arrow that points side to side) or vice versa. In some aspects, the second depth adjustment slot 441 has thinned regions 496 proximate a second engagement surface 442 that engage a second set of locking faces 444a, 444b on the second male chin rivet 443. The second male chin rivet 443 may further comprise second male chin rivet notches 498a, 498b that may be aligned with one of the second chin depth sizing indicia 446, when unlocked, if desired. Once the desired depth adjustment is made, the second male chin rivet indicator 497 may be moved to the locked position (such as an arrow that points up and down). Collectively, these components may be referred to as the second chin rest locking mechanism.

Rivets referred to herein generally may comprise a male portion and a female portion or may comprise an integral connecting mechanism. Other couplers that are suitable to replace the rivets, such as comprising screws, nuts, bolts, pins, flanges, buttons, or buckles; and conventional locking mechanisms that can fix the chin rest into position, are contemplated.

The body portion 170 may comprise a first lateral body portion 184 having a first body elongate slot 187 for receiving a first body sliding rivet 416; and a second lateral body portion 194, having a second body elongate slot 197 for receiving a second body sliding rivet 426.

Posterior components are recited in the art in, for example, U.S. Pat. Nos. 9,414,956, 8,932,243, 6,494,854, 6,872,188, 9,713,546, 8,858,481, 9,668,906, 7,981,068, and 8,679,044. Conventionally an anterior component and a posterior component may be coupled together to form a cervical collar, such as through slots at the back portion of the anterior component through which a hook and loop strap may be attached. Posterior and anterior components may comprise substantially rigid materials.

Referring to FIGS. 21-27, embodiments of a cervical collar comprise an anterior component 100 coupled to a posterior component 500 using various strap and attaching mechanisms. In some aspects, the attaching mechanisms allow a medical professional to make adjustments to the circumference of the cervical collar to fit a user with a user-specific neck circumference, while allowing the removal of the cervical collar, for example by the patient in a home setting, and then redonning while maintaining the same circumferential configuration after it is redonned without readjusting the circumference.

In one embodiment, some portions of the first attaching mechanism 501 (e.g., FIG. 24), may be found on the anterior component 100 and some portions may be found on the posterior component 500.

Regarding some aspects in FIGS. 23-34, portions of the first attaching mechanism 501 may be found on the anterior component 100. The anterior component 100 may comprise a first anterior mating piece 510 for mating to a first posterior mating piece 520 on the posterior component 500. The first anterior mating piece 510 may comprise an optional first anterior housing 511 and a first anterior coupler 512 disposed therein, such as a hook and loop coupler, pressure sensitive adhesive (PSA), interlocking parts such as a buckle or mated shapes, cord/cable tied off or looped to a post, or, if the material does not need to be radiolucent, magnets.

Similarly, in some aspects, the anterior component 100 may also comprise a second anterior mating piece 515 (not shown) for mating to a second posterior mating piece 530 (not shown) on the posterior component 500. The second anterior mating piece 515 (not shown) may comprise an optional second anterior housing 516 (not shown) and a second anterior coupler 517 (not shown) disposed therein, such as a hook and loop coupler, pressure sensitive adhesive (PSA), interlocking parts such as a buckle or mated shapes, cord/cable tied off or looped to a post, or if the material does not need to be radiolucent, magnets.

These couplers may be used in other strap or attaching mechanisms herein.

In some aspects, the first anterior mating piece 510 is configured so as to easily align and couple it with the first posterior mating piece 520 on the posterior component 500. Similarly, the second anterior mating piece 515 (not shown) is configured so as to easily align and couple it with the second posterior mating piece 530 (not shown) on the posterior component 500.

Thus, for example, a posterior mating piece may comprise hook material, while an anterior mating piece may comprise loop material, or vice versa. Other couplers are contemplated such as snaps, buckles and other complementary couplers, which may be also useful for other embodiments herein.

The optional anterior housings 511, 516 if present, may be molded into, and may be integral with, the anterior component 100 or attached using conventional attachment means such as a rivet or adhesive. In some embodiments, a first anterior mating piece 510 and second anterior mating piece 520 is attached to each lateral side of an anterior component proximate the lateral sides of the posterior component when in use.

In some aspects, the first posterior mating piece 520 on the posterior component 500 may comprise a first posterior coupler 522 such as a hook and loop coupler that is configured to be received by the first anterior mating piece 510, and may contain an optional first posterior housing 521 (not shown). The first posterior mating piece 520 may further comprise a first slot 523 for receiving a first fixed hook and loop strap 524.

Similarly, in some aspects, the second posterior mating piece 530 (not shown) on the posterior component 500 may comprise a second posterior coupler 532 (not shown) such as a hook and loop coupler that is configured to be received by the second anterior mating piece 515 (not shown), and may contain an optional second posterior housing 531 (not shown). The second posterior mating piece 530 (not shown) may further comprise a second slot 533 for receiving a second fixed hook and loop strap 534.

The slots 523, 533 may have dimensions to receive a hook and loop strap. Fixed hook and loop straps 524, 534 may be integral with, such as by molding, or otherwise permanently attached to the posterior mating pieces 520, 530 such as by sonic welding, sewing, clamping or gluing. "Permanently attached" is not intended to refer to absolute permanence but rather to distinguish an attachment that is relatively more difficult to attach and reattach.

In some aspects, the fixed hook and loop straps 524, 534 are configured so that they each may be passed through a portion of the back panel 503 such as through slots 504a, 504b and can attach to itself. In some aspects when in use, a medical professional may attach the posterior mating pieces 520, 530 to the respective anterior mating pieces 510, 515, and adjust the fixed hook and loop straps 524, 534 to fit the neck circumference of a user. Once the circumference is prescribed the fixed hook and loop straps 524, 534 (and other straps if present) are not adjusted. Thus, to doff the collar, the patient detaches the posterior mating pieces 520, 530 from the anterior component. To don the collar the patient reattaches the posterior mating pieces 520, 530 without adjusting the strap lengths.

In some aspects, the first posterior mating piece 520 may also comprise a first removable hook and loop strap 525 that may attach to the distal end of the first fixed hook and loop strap 524 to extend the length of the strap to fit larger necks. Similarly, the second posterior mating piece 530 (not shown) may also comprise a second removable hook and loop strap 535 (not shown) that may attach to the distal end of the second fixed hook and loop strap 534 (not shown) to extend the length of the strap to fit larger necks. If present, the removable hook and loop strap 525, 535 can be removed to fit smaller necks.

In some aspects, the first posterior mating piece 520 may also comprise a first intermediate removable hook and loop strap 526 (not shown) that may attach to the distal end of the first removable hook and loop strap 525 and/or first fixed the hook and loop strap 524 to extend the length of the strap to fit larger necks or to provide versatility with respect to lengths. Similarly, the second posterior mating piece 530 (not shown) may also comprise a second intermediate removable hook and loop strap 536 (not shown) that may attach to the distal end of the second removable hook and loop strap 535 and/or second fixed the hook and loop strap 534 to extend the length of the strap to fit larger necks or to provide versatility with respect to lengths A radiolucent modular strapping system without a back panel is also contemplated. In some aspects the modular strapping system may comprise the anterior mating piece 510 and posterior mating piece 520 the fixed hook and loop straps 524, the removable hook and loop strap 525, and/or the intermediate removable hook and loop straps 526. The strapping system may be useful with conventional cervical collar components, wherein the anterior mating piece 510 may in some aspects comprise a retrofit coupler (such as adhesive or bonding material) for coupling to an anterior component. The modular strapping system may comprise two identical anterior and posterior mating pieces for attaching to each lateral side of an anterior component.

The fixed hook and loop straps 524, 534, the removable hook and loop strap 525, 535, and intermediate removable hook and loop straps 526, 536, and other straps herein, each may have a length of about 4-9 inches, and be able to accommodate a total lengths about 4-9 inches when used alone, or in various combinations. The fixed hook and loop straps 524, 534, the removable hook and loop strap 525, 535, intermediate removable hook and loop straps 526, 536, and other straps herein, each may have a width of about 1-2 inches.

In another embodiment of a strapping and attaching mechanism, a cam surface assembly may be rotated one direction, wherein the cam pulls the strap along the cam groove. When rotated the other direction the strap is loosened and the cam assembly can be removed. Thus, posterior component can be removed and reattached without disturbing the circumferential dimensions as fitted by the medical professional as recited herein.

Figure 21:
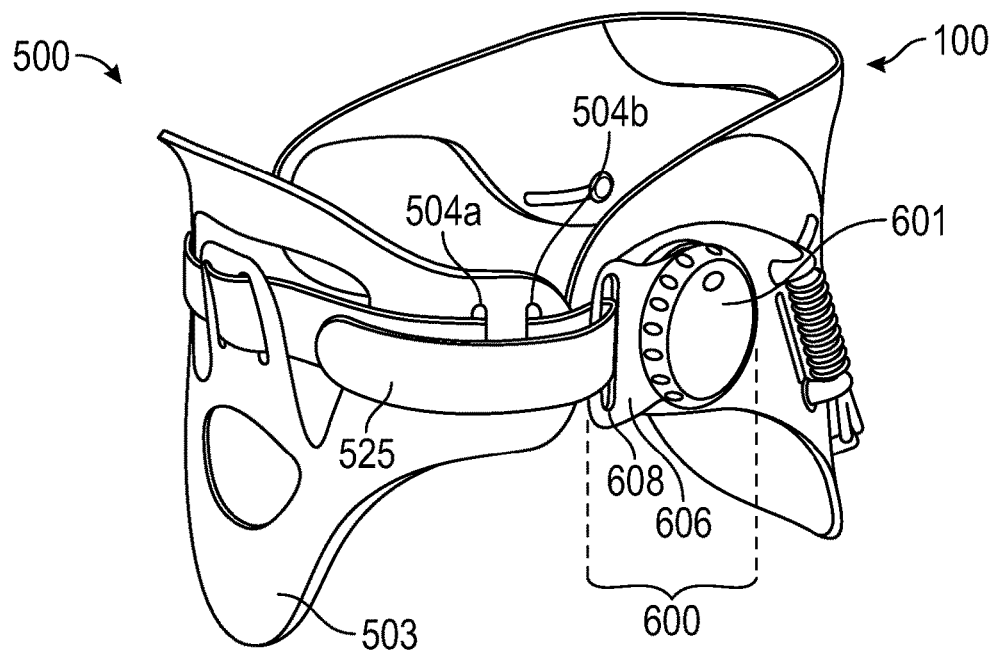
FIG. 21 is a perspective view of an embodiment of a cervical collar with the cam surface assembly attached to an anterior component and engaging a strap of the posterior component of the cervical collar.
Figure 22:
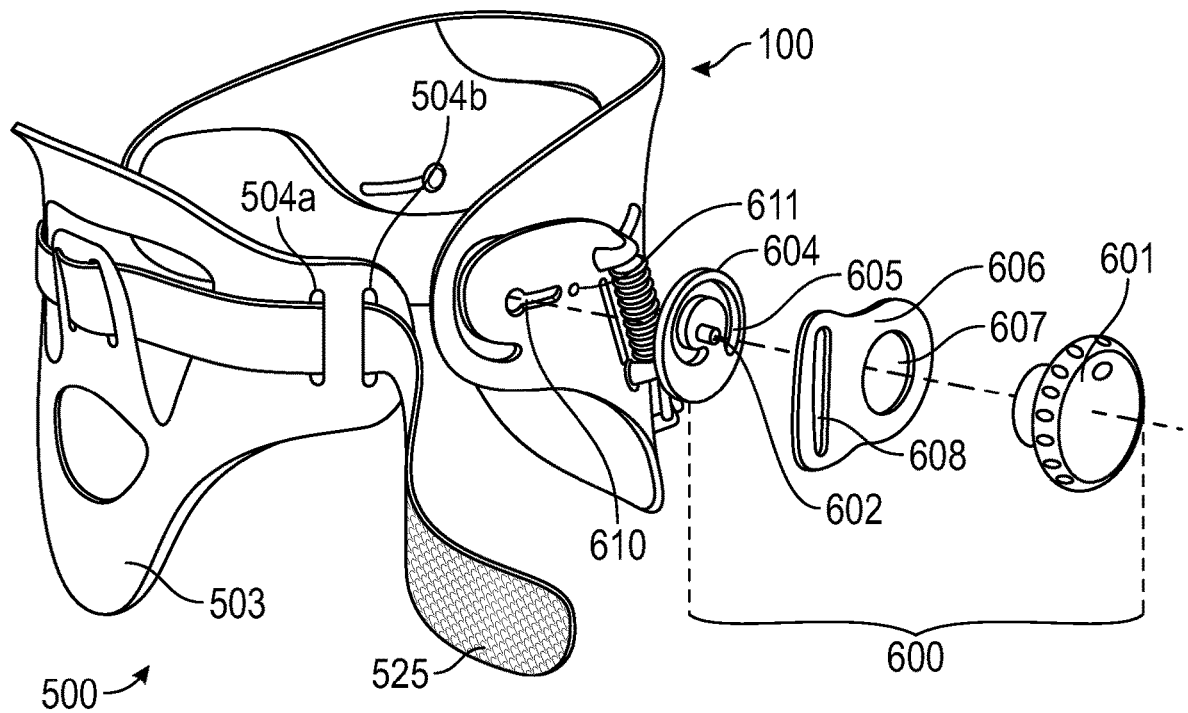
FIG. 22 is an exploded view of an embodiment of the cam surface assembly detached from an anterior component and posterior component of a cervical collar.
Figure 24A:
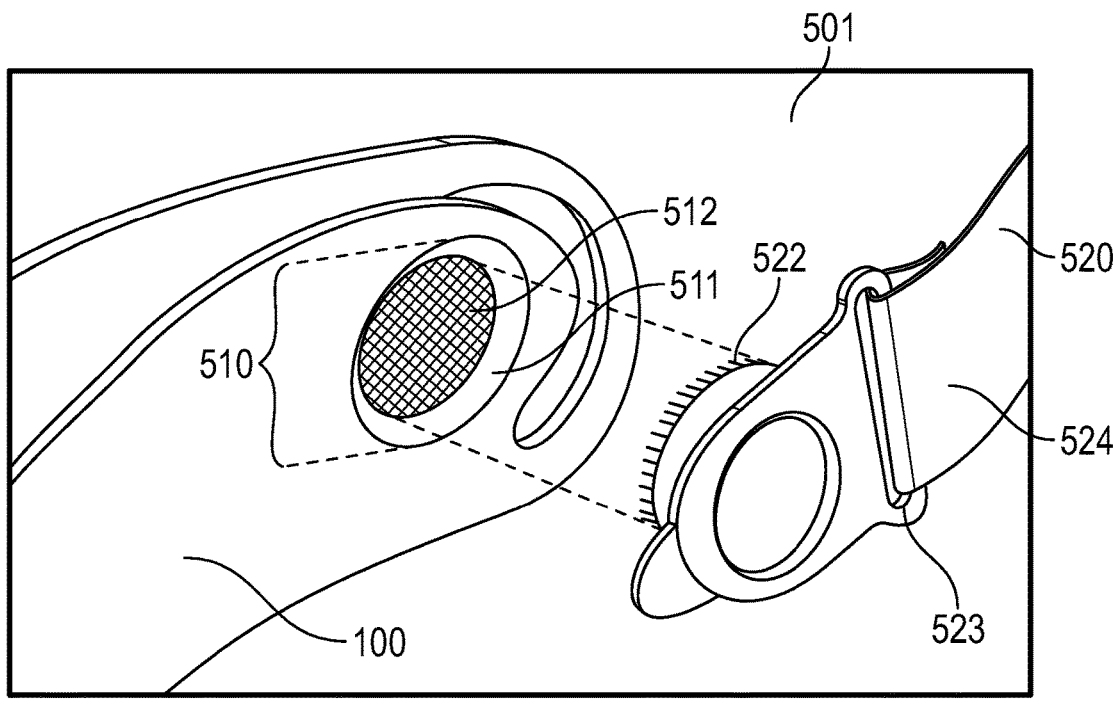
FIG. 24a and FIG. 24b illustrate of an embodiment the attachment mechanism of an adjustable posterior component of a cervical collar.
Figure 24B:
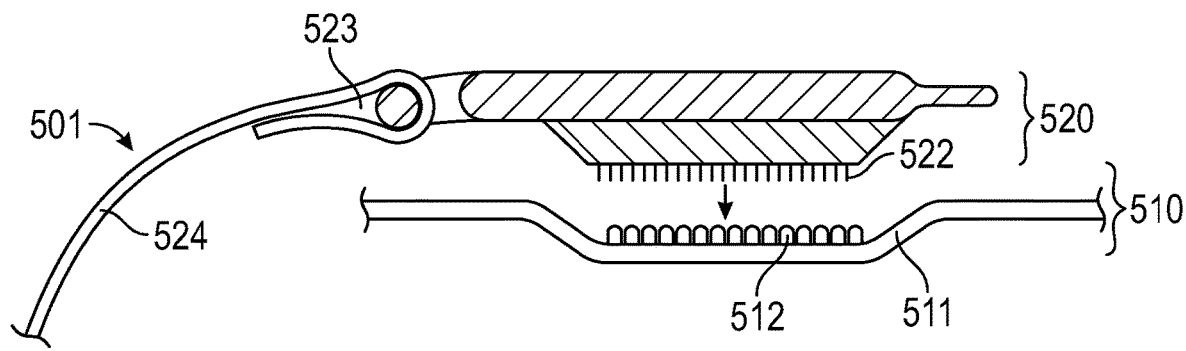

Referring to FIGS. 21-22, an embodiment of a cervical collar may comprise an anterior component 100 coupled to a posterior component 500, using a conventional hook and loop strap 525 removably attached to a back panel 503 through slots such as 504a, 504b therein. Modular straps, recited further herein (e.g., FIG. 23), with a removable strap portion 525 may also be used in this and other embodiments.

A first cam surface assembly 600 may comprise a first cam actuator 601, a first follower 611 that engages a first cam groove 605 in a first cam surface carrier 604. The first cam surface carrier 604 has a first post 602 that is received by an opening (not shown) of the first cam actuator 601 to form the first cam surface assembly 600. The first cam surface carrier 604, opposite the side having the first post 602, may have a first keyhole post 609 (not shown). In some aspects, the first keyhole post 609 (not shown), may engage a first keyhole 610 on the anterior portion 100.

Similarly, if two cam surface assemblies 600 are present, such as on both lateral sides of the cervical collar to promote ambidextrous use, a second cam surface assembly 620 (not shown) may comprise a second cam actuator 621 (not shown), a second cam follower 631 (not shown) that engages a second cam groove 625 (not shown) on a second cam surface carrier 624 (not shown). The second cam surface carrier 624 (not shown), has a second post 622 (not shown) that is received by an opening of the second cam actuator 621 (not shown) to form the second cam surface assembly 620 (not shown). The second cam surface carrier 624 (not shown), opposite the side having the second post 622 (not shown), may have a second keyhole post 629 (not shown). In some aspects, the second keyhole post 629 (not shown), may engage a second keyhole 630 (not shown) on anterior component 100.

In some aspects, couplers other than posts and keyholes are also contemplated. For example each of the cam surface carriers 604, 624 may have a base with a cam follower 611, 631 that may be adhered to the anterior component such as with adhesive, or hook and loop material. Also, the base for the cam surface carriers 604, 624 may be welded onto or molded into the anterior component.

In some aspects, positioned between the first cam actuator 601 and first cam surface carrier 604 may be a first freely rotating strap holder 606, having a first opening 607 that allows the cam actuator 601 to engage the first post 602 on the cam surface carrier 604 and allows the strap holder 606 to traverse linearly when the first cam actuator 601 is rotated by a user. In some aspects, the first rotating strap holder 606 may comprise a first slot 608 for receiving a hook and loop strap 525.

Similarly, if two cam surface assemblies 600, 620 are present, positioned between the second cam actuator 621 and second cam surface carrier 624 may be a second freely rotating strap holder 606, having a second opening 627 that allows the second cam actuator 621 to engage the second post 622 on the second cam surface carrier 624 and allows the strap holder 626 to traverse linearly when the second cam actuator 621 is rotated by a user. (Second cam assembly not shown.)

In some aspects, the second rotating strap holder 626 may comprise a second slot 608 for receiving the other end of the hook and loop strap 525 or a different hook and loop strap, such as a modular strap recited herein (not shown in FIGS. 21-22).

In some aspects, the hook and loop strap 525 is configured so that they each may be passed through a portion of the back panel 503 such as through slots 504a, 504b and can attach to itself. Once the circumference is prescribed, the fixed hook and loop straps 525 (and other straps if present, such as with a modular strapping system) are not adjusted. In some aspects, when in use, the medical professional can fit the patient's neck circumference with the cam surface assembly 600 in the tightened position (or both tightened if two are present) by adjusting either ends of the hook and loop strap 525, which have been pulled through slot 608 and a slot on the anterior component, onto itself. When the patient is ready to doff the cervical collar, the cam actuator 601 may be loosened, the keyhole post 609 removed from the keyhole 610, and the posterior component 500 disconnected from the anterior component 100 without disturbing the strap placement made to accommodate the unique neck circumference set by the medical professional. Upon redonning, the patient can engage the keyhole post 609 with the keyhole 610 on the anterior component 100 and tighten to achieve the fit originally provided by the medical professional.

The rotational motion of the cam actuator 601 linearly pulls the strap slightly tighter, such as about ¼-1 inch tighter or about ½inch. In some aspects, the cam rotation may be about 270° to pull about ½inch, and cam actuator 601 can be manufactured to accommodate different tightening lengths and rotation. In some aspects the cam actuator 601 is tightened by rotating it forward to tighten it (and backward to loosen), although it can be disposed such that it can tighten and loosen in the opposite direction.

Referring to FIGS. 25-28, embodiments a cervical collar may comprise a strap alignment mechanism that facilitates the attachment of the posterior component 500 to the anterior component 100. For example, in some aspects, cervical collar may contain two lateral strap alignment mechanisms comprising straps 701, 711 that are looped through a plurality of slots 504 in the back panel 503 of the posterior component 500. In some aspects, the strap alignment mechanism allows a medical professional to make adjustments to the circumference of the cervical collar to fit a user with a user-specific neck circumference, while allowing the removal of the cervical collar, for example by the patient in a home setting, and providing alignment indicia so that the same circumferential configuration can be reproducibly aligned upon redonning.

In some aspects, a first collar indicium 702 for aligning the strap alignment mechanism may be found on the first lateral body portion 184 of the anterior component 100 that corresponds to the strap indicium 703 on the first strap 701. In some aspects, for example, a loop portion on the first strap 701 fastens to a first hook portion 708 on the first lateral body portion 184 of the anterior component 100, or vice versa. A first collar indicium 702 on first lateral body portion 184 of the anterior component 100 may be aligned with a first strap indicium 703 on the first strap 701 so that the neck circumference can be reproducibly aligned. Similarly, on the other side of the collar, a second collar indicium 712 for aligning the strap alignment mechanism may be found on the second lateral body portion 194 of the anterior component 100 that pairs with second strap indicium 713 (not shown) on the second strap 711. In some aspects, for example, a loop portion on the second strap 711 fastens to a second hook portion 718 (not shown) on the second lateral body portion 194 of the anterior component 100, or vice versa. A second collar indicium 712 (not shown) on second lateral body portion 194 of the anterior component 100 may be aligned with a second strap indicium 713 (not shown) on the second strap 711 so that the neck circumference can be reproducibly aligned.

The edge of the loop end proximate the anterior ends 705, 715 may comprise a hardened area, which may be made by melting the loop material to form a finger grips 704, 714 (not shown) so that the ends may be easily grasped by the user to remove the collar.

On the first posterior end 706 of the strap 701, hook material on one end may be connected to the loop material on the first strap 701, to make a fastening area proximate the back panel 503 of the posterior component 500 when connected thereto. Thus, when the hook material is looped through slots 504 on the posterior component 500 of the cervical collar, the hook material of the first strap 701 can fold upon itself to join the loop material on the same first strap 701.

Similarly, on the other side, the second posterior end 716 of the second strap 711, hook material on one end may be connected to the loop material on the second strap 711, to make a fastening area proximate the back panel 503 of the posterior component 500 when connected thereto. Thus, when the hook material is looped through slots 504 on the posterior component 500 of the cervical collar, the hook material of the second strap 711 can fold upon itself to join the loop material on the same second strap 711.

Figure 25:
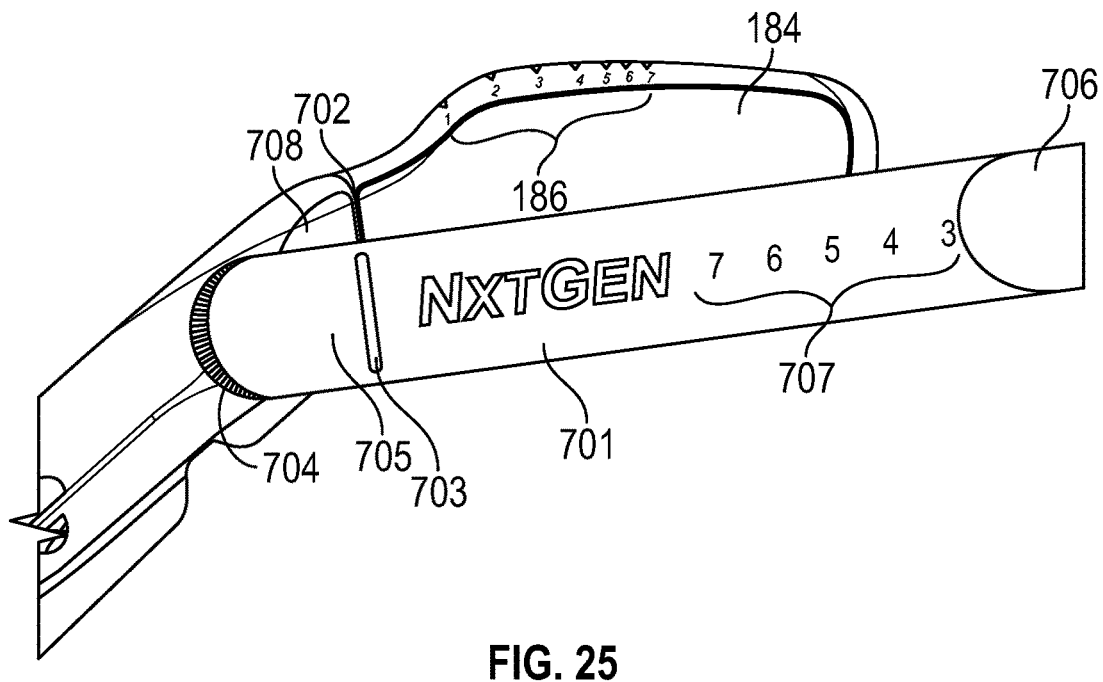
FIG. 25 is a perspective view of an embodiment of a strap alignment mechanism of a cervical collar in the foreground and a portion of an anterior component in the background.
Figure 26:
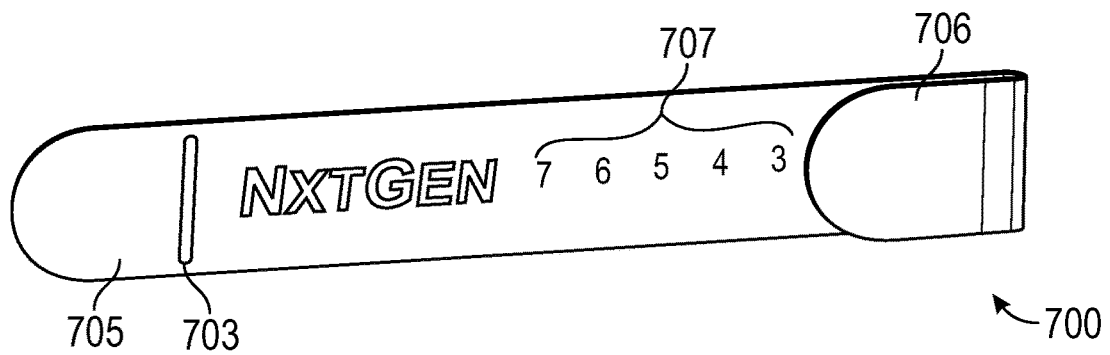
FIG. 26 illustrates an embodiment of sizing indicia with numbers on the strap.
Figure 27:
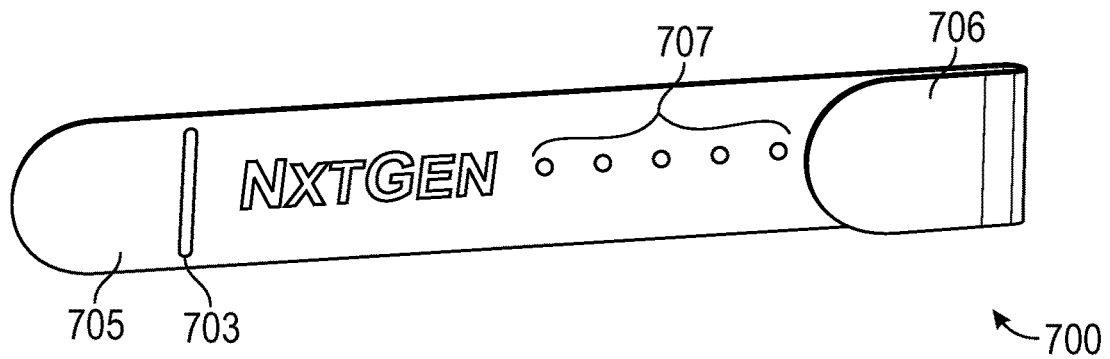
FIG. 27 illustrates an embodiment of sizing indicia with dots on the strap.
Figure 28A:
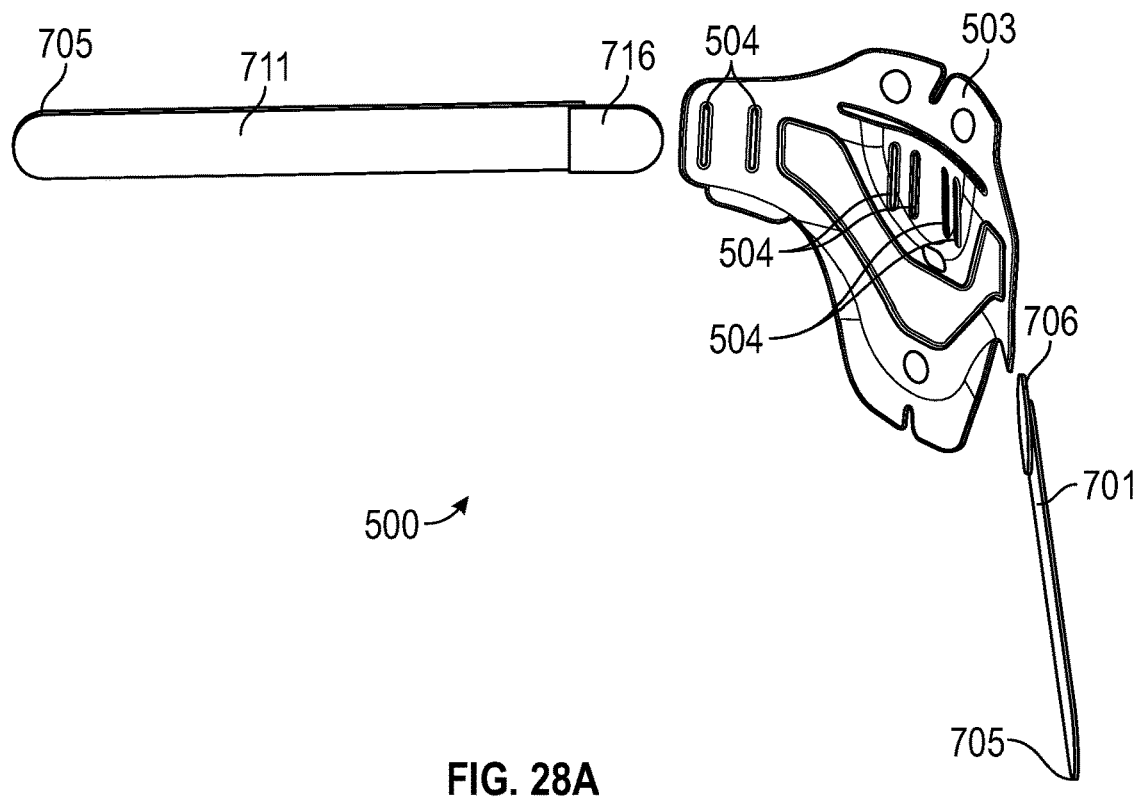
FIG. 28a is a perspective view of an embodiment of a posterior component with straps.
Figure 28B:
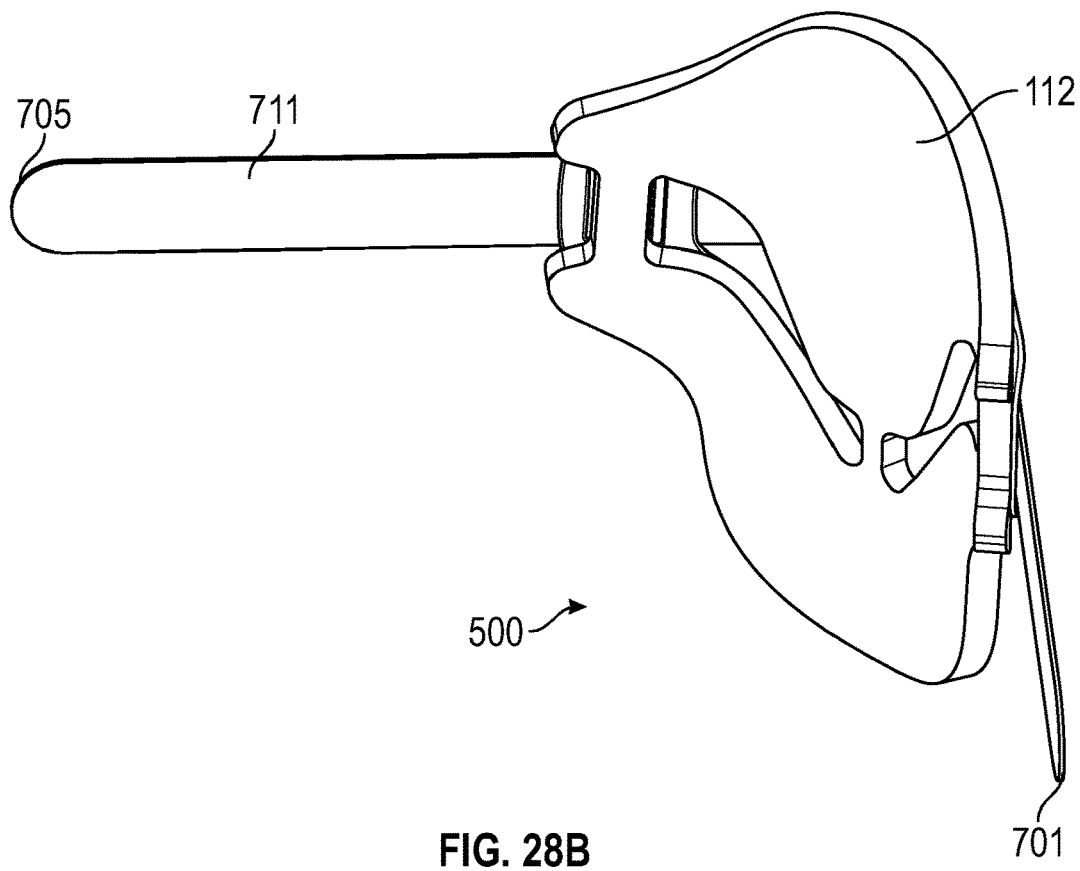
FIG. 28b is a perspective view of an embodiment of a posterior component with straps assembled and with foam padding.

A medical professional may make a gross adjustment of the circumference proximate the back panel 503 of the posterior component 500 by adjusting the hook portions of each of the straps 701, 711 over the loop portions on each. The straps may comprise sizing indicia 707, 717 (not shown) such as numbers (FIGS. 25-26) or dots (FIG. 27) that will allow a prescription to be written (such as a size "3" as shown in FIGS. 25-26) facilitating a medical professional or user to make a gross adjustment of the circumference of the cervical collar to the prescribed position.

The straps herein, such as, 701, 711 may comprise loop material, while a mating portion on the lateral body portions 184, 194 of the anterior component 100 may comprise hook material, or vice versa as long as the sides mate. Other couplers are contemplated such as snaps, buckles and other complementary couplers. Straps herein, such as, 701, 711 may be used with modular straps, such as a removable strap portion 525 may recited herein. Straps herein, such as, 701, 711 may be used with modular straps, such as a removable strap portion 525 (FIG. 23) recited herein.

Slots 504 on the posterior component may have dimensions to receive a connector such as a hook and loop straps 701, 711.

The anterior component 100 may include a housing or mechanism enclosure 111 (FIG. 29) that may include an external fitting or knob 476. In some aspects, the housing 111 may include an opening 477 for receiving the internal knob or drive gear 470.

The components herein such as the anterior component 100, posterior component 500, housing or mechanism enclosure 111, one-piece shell 110, lead screw mechanism, latching mechanism, four bar adjustment mechanism, posterior mating pieces 520, 530, cam surface assemblies 600, 620 and/or portions thereof have appropriate properties such as fatigue properties and/or plastic deformation point suitable for cervical collar purposes. In some aspects, the components or portions may be made from materials including a substantially rigid material or semi rigid and made from radiolucent material. Such materials include, for example, injection molded and may include, for example, acrylonitrile butadiene styrene (ABS), polyester, copolyester, polyethylene terephthalate (PET), polybutylene terephthalate (PBT), polyoxymethylene (POM), styrene acrylonitrile copolymer (SAN), polycarbonate (PC), copolycarbonate, polycarbonate blends i.e., PC and (ABS, polyester, copolyester, SAN, PET, PBT, POM, and/or SAN), or other blends thereof.

In some aspects the components herein such as the anterior component 100, posterior component 500, one-piece shell 110, posterior mating pieces 520, 530, cam surface assemblies 600, 620 or portions thereof, may be overmolded to provide a soft touch or pressure fingers with the following materials: natural or synthetic polyisoprene, polybutadiene, chloroprene rubber (CR), polychloroprene, butyl rubber (copolymer of isobutylene and isoprene, IIR), halogenated butyl rubbers, styrenebutadiene rubber (copolymer of styrene and butadiene, SBR), nitrile rubber (copolymer of butadiene and acrylonitrile, NBR), hydrogenated nitrile rubbers (HNBR), EPM (ethylene propylene rubber, a copolymer of ethylene and propylene), EPDM rubber (ethylene propylene diene rubber, a terpolymer of ethylene, propylene and a diene-component), epichlorohydrin rubber (ECO), polyacrylic rubber (ACM, ABR), silicone rubber (SI, Q, VMQ), fluorosilicone rubber (FVMQ), fluoroelastomers (FKM, and FEPM), perfluoroelastomers (FFKM), polyether block amides (PEBA), chlorosulfonated polyethylene (CSM), ethylene-vinyl acetate (EVA), and/or thermoplastic elastomers (TPE). In some aspects, the anterior component 100, posterior component 500 and/or four bar adjustment mechanism, or portions thereof, may be made of more rigid versions of the overmolding materials listed above.

In some aspects, the height adjustment mechanism 200 does not contain a gear mechanism. In some aspects, the single adjustment mechanism 200 does not comprise a rack and pinion, wherein a rack cooperates with a pinion. In some aspects, the single adjustment mechanism 200 does not comprise a cable or a pulley. In some aspects the chin portion and the body portion are not pivotally coupled. In some aspects, the chin portion and the body portion are not supported only on ends of the chin portion and the body portion. In some aspects, the chin portion is unable to bend to fit a user's chin contours when in use, and is therefore, sufficiently stiff, rigid, or semi rigid to prevent different user's chin contours to adjust the shape of the chin portion when in use. In some aspects, the chin piece may be sufficiently semi rigid and has some flexibility so that it can retain its approximate initial shape before donning the collar and after it has been donned regardless of the contours of various users' chins.

The adjustable anterior component 100 may be coupled to a posterior component to form a cervical collar with a coupler such as through slots 504 (see FIGS. 28-29) proximate the distal ends of the lateral chin portions 135, 145 and/or lateral body portions 184, 194 through which a hook and loop strap may be secured.

Any of the anterior components 100 herein may be coupled to any suitable posterior component, such as posterior component 500, to form a cervical collar with a coupler such as hook and loop material attached to the lateral body portion 184, and/or through slots 504 on the posterior component 500, and/or through slots proximate the ends of the anterior component 100, such as proximate the deforming portions 160, 161 (FIG. 1-5, slots not shown) through which a hook and loop strap may be secured.

In addition to the components herein, additional portions such as foam 112 (FIGS. 28b and 29) and/or slots 504 for receiving straps for attaching the components to form a cervical collar are also contemplated.

A portion as used herein may refer to a portion of the one-piece shell, if present, a portion of the cervical collar, or a portion of a component.

The terms "approximately" "about" and "substantially" as used herein represent an amount or configuration close to the stated amount or configuration that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

All documents referenced herein are hereby incorporated by reference into this application.

We claim:

1. A cervical collar comprising:
an anterior component comprising:
a chin portion,
a body portion, and
a four bar adjustment mechanism configured to raise and lower the chin portion substantially vertically, wherein a single adjustment of the four bar adjustment mechanism raises and lowers lateral sides of the chin portion relative to the body portion, the four bar adjustment mechanism comprising:
a first pair of cross bars positioned laterally on a first side of the anterior component between the chin portion and the body portion;
a first lead screw positioned laterally on the first side of the anterior component and coupled between a drive gear and a first cross bar of the first pair of cross bars;
a second pair of cross bars positioned laterally on a second side of the anterior component between the chin portion and the body portion; and
a second lead screw positioned laterally on the second side of the anterior component and coupled between the drive gear and a first cross bar of the second pair of cross bars.

2. The cervical collar of claim 1, wherein the first lead screws is rotatably coupled to a first shuttle and the second lead screw is rotatably coupled to a second shuttle.

3. The cervical collar of claim 2, wherein the first shuttle is coupled to a first end of a first actuator bar and the second shuttle is coupled to a first end of a second actuator bar.

4. The cervical collar of claim 3, wherein:
a second end of the first actuator bar is coupled to a first end of the first cross bar of the first pair of cross bars; and
a second end of the second actuator bar is coupled to a first end of the first cross bar of the second pair of cross bars.

5. The cervical collar of claim 4, wherein the chin portion comprise a first lateral chin portion and a second lateral chin portion, each defining a respective elongate slot therein.

6. The cervical collar of claim 5, wherein the body portion comprises a first lateral body portion and a second lateral body portion each defining a respective elongate slot therein.

7. The cervical collar of claim 6, wherein the coupled second end of the first and second actuator bars are each configured to ride in the respective elongate slot in the first or second lateral body portion.

8. The cervical collar of claim 7, wherein a first end of a second cross bar of each of the first and second pairs of cross bars is configured to ride in the respective elongate slot in the first or second lateral chin portion.

9. The cervical collar of claim 8, wherein:
a second end of the second cross bar of each of the first and second pairs of cross bars is rotatably coupled in a stationary position to a respective one of the first and second lateral body portions; and
wherein a second end of the first cross bar of each of the first and second pairs of cross bars is rotatably coupled in a stationary position to a respective one of the first and second lateral chin portions.

10. The cervical collar of claim 1, wherein an end of each of the first and second lead screws comprises a respective bevel gear that engages the drive gear.

11. The cervical collar of claim 5, wherein the chin portion comprises:
a chin rest movably coupled to and disposed between the first and second lateral chin portions; and
a chin depth adjustment mechanism configured to provide substantially horizontal movement of the chin portion with respect to the first and second lateral chin portions.

12. The cervical collar of claim 11, wherein the first and second lateral chin portions each comprises a respective substantially horizontal depth adjustment slot for receiving a respective coupler positioned on a respective end of the chin rest.

13. The cervical collar of claim 12, wherein each of the respective couplers comprises a rivet.

14. The cervical collar of claim 11, wherein the chin rest is configured to pivot.

* * * * *